US005612985A

United States Patent [19]
Toki et al.

[11] Patent Number: 5,612,985
[45] Date of Patent: Mar. 18, 1997

[54] COMPUTER TOMOGRAPHY APPARATUS

[75] Inventors: Yusuke Toki, Utsunomiya; Manabu Hiraoka, Nishinasunomachi; Ichiro Yamagishi, Otawara; Hiroyuki Onuki, Tochigi-ken; Tatsuya Ban, Utsunomiya; Tetsuro Hada, Otawara; Takeo Nabatame, Tochigi-ken; Masao Yamahana, Otawara; Masakuni Fujise, Otawara; Yoshihiko Aochi, Otawara; Makoto Hayashibara, Tochigi-ken; Masahiro Ozaki, Otawara, all of Japan

[73] Assignee: Kabushiki Kaisha Toshiba, Kawasaki, Japan

[21] Appl. No.: 547,144

[22] Filed: Oct. 24, 1995

Related U.S. Application Data

[62] Division of Ser. No. 347,135, Nov. 23, 1994.

[30] Foreign Application Priority Data

Nov. 26, 1993 [JP] Japan .................. 5-297079
Apr. 5, 1994 [JP] Japan .................. 6-067343
Oct. 31, 1994 [JP] Japan .................. 6-267280

[51] Int. Cl.⁶ ............................ A61B 6/03
[52] U.S. Cl. ................... 378/4; 378/8; 378/20
[58] Field of Search ............... 378/4, 8, 15, 19, 378/20, 95, 118

[56] References Cited

U.S. PATENT DOCUMENTS

| | | | |
|---|---|---|---|
| 4,477,923 | 10/1984 | Baumann et al. | 378/95 |
| 4,991,193 | 2/1991 | Cecil et al. | 378/117 |
| 5,377,250 | 12/1994 | Hu | 378/15 |
| 5,383,231 | 1/1995 | Yamagishi | 378/15 |
| 5,412,702 | 5/1995 | Sata | 378/4 |
| 5,459,769 | 10/1995 | Brown | 378/4 |

Primary Examiner—David P. Porta
Attorney, Agent, or Firm—Oblon, Spivak, McClelland, Maier & Neustadt, P.C.

[57] ABSTRACT

A computer tomography apparatus of the present invention can select one of an ON state in which X-ray radiation is performed to continuously acquire projection data and an OFF state in which acquisition of projection data is stopped, and even in the OFF state, rotation of an X-ray tube is continued, thus allowing quick switching from the OFF state to the ON state.

22 Claims, 23 Drawing Sheets

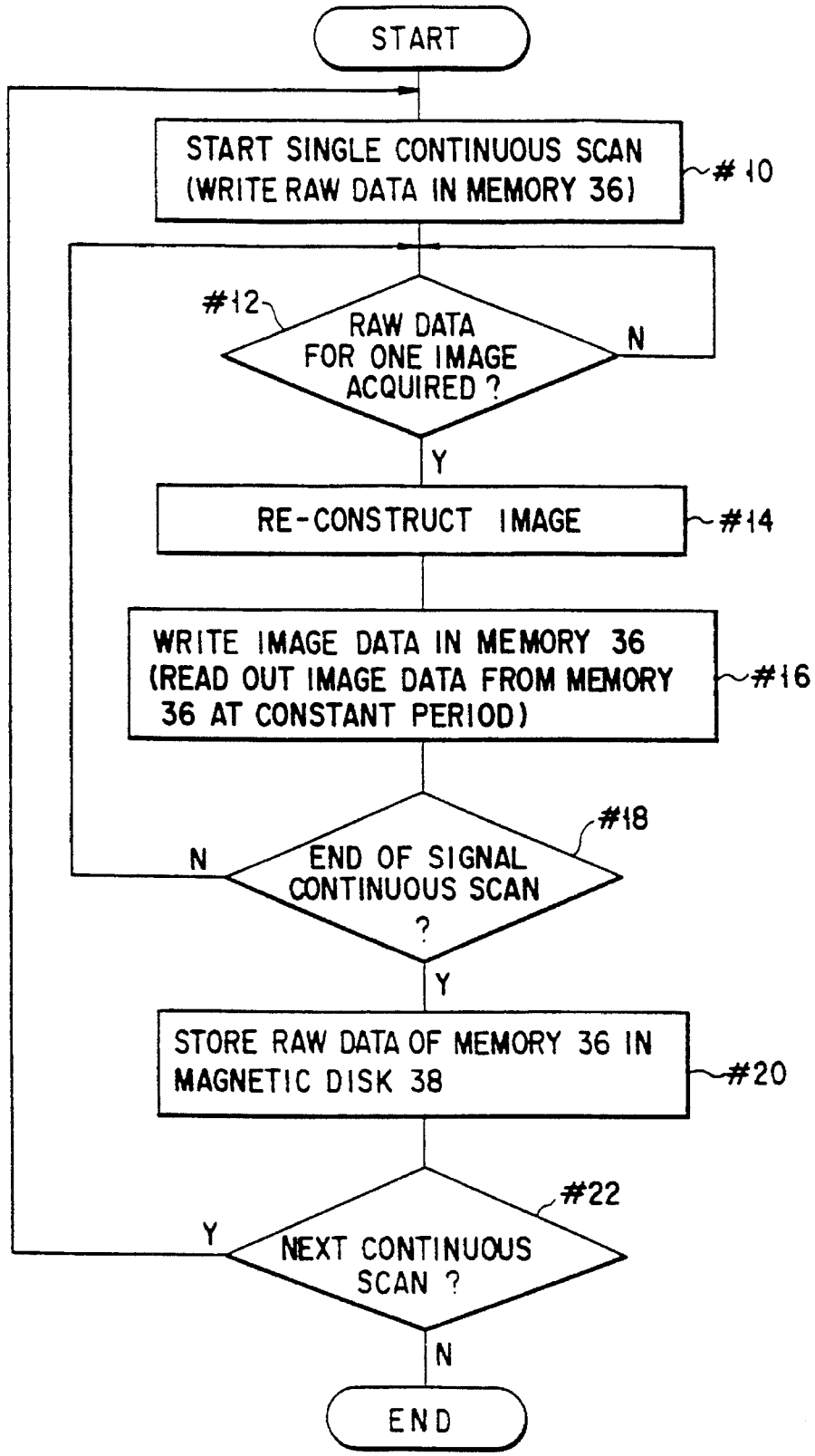
F I G. 1

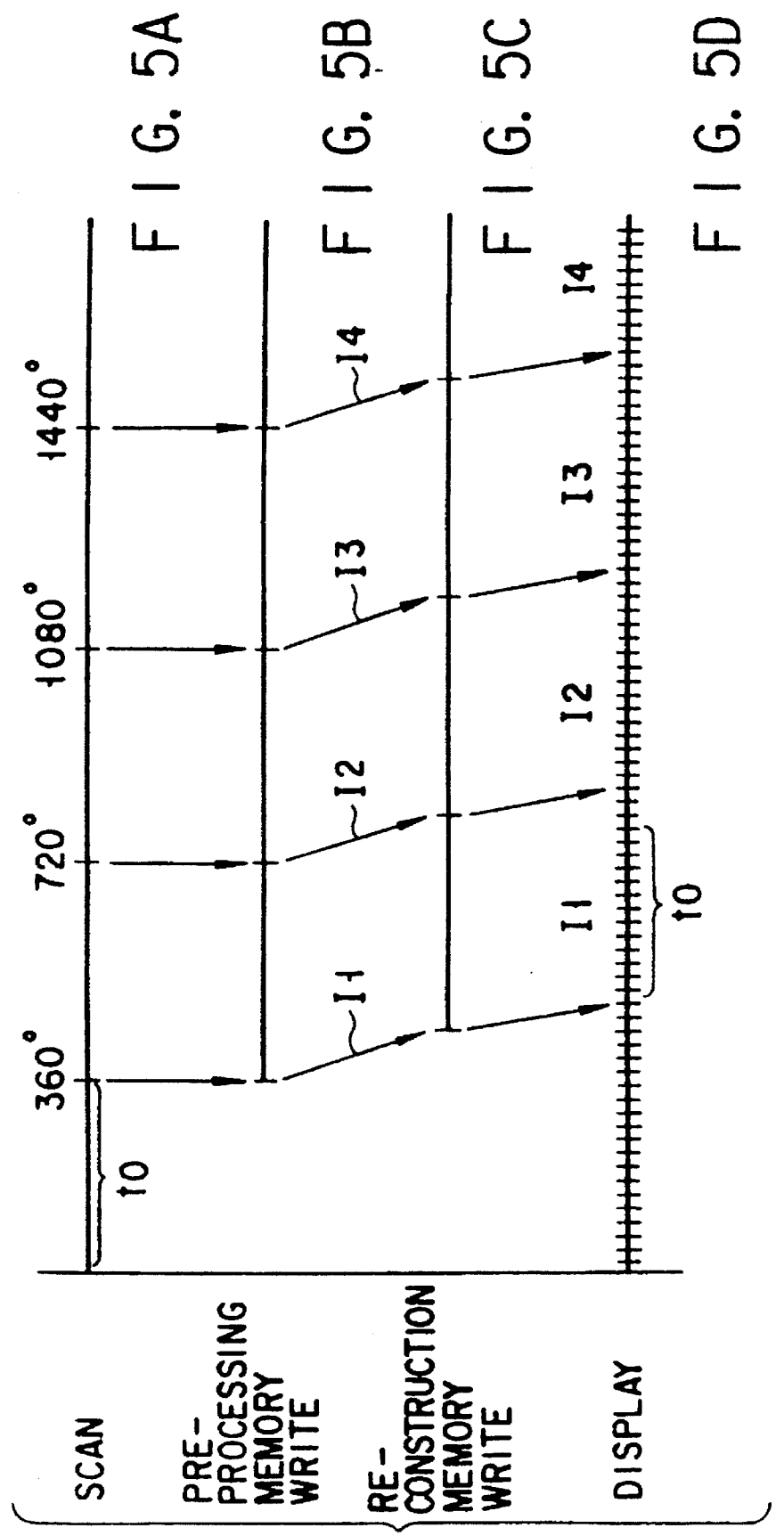

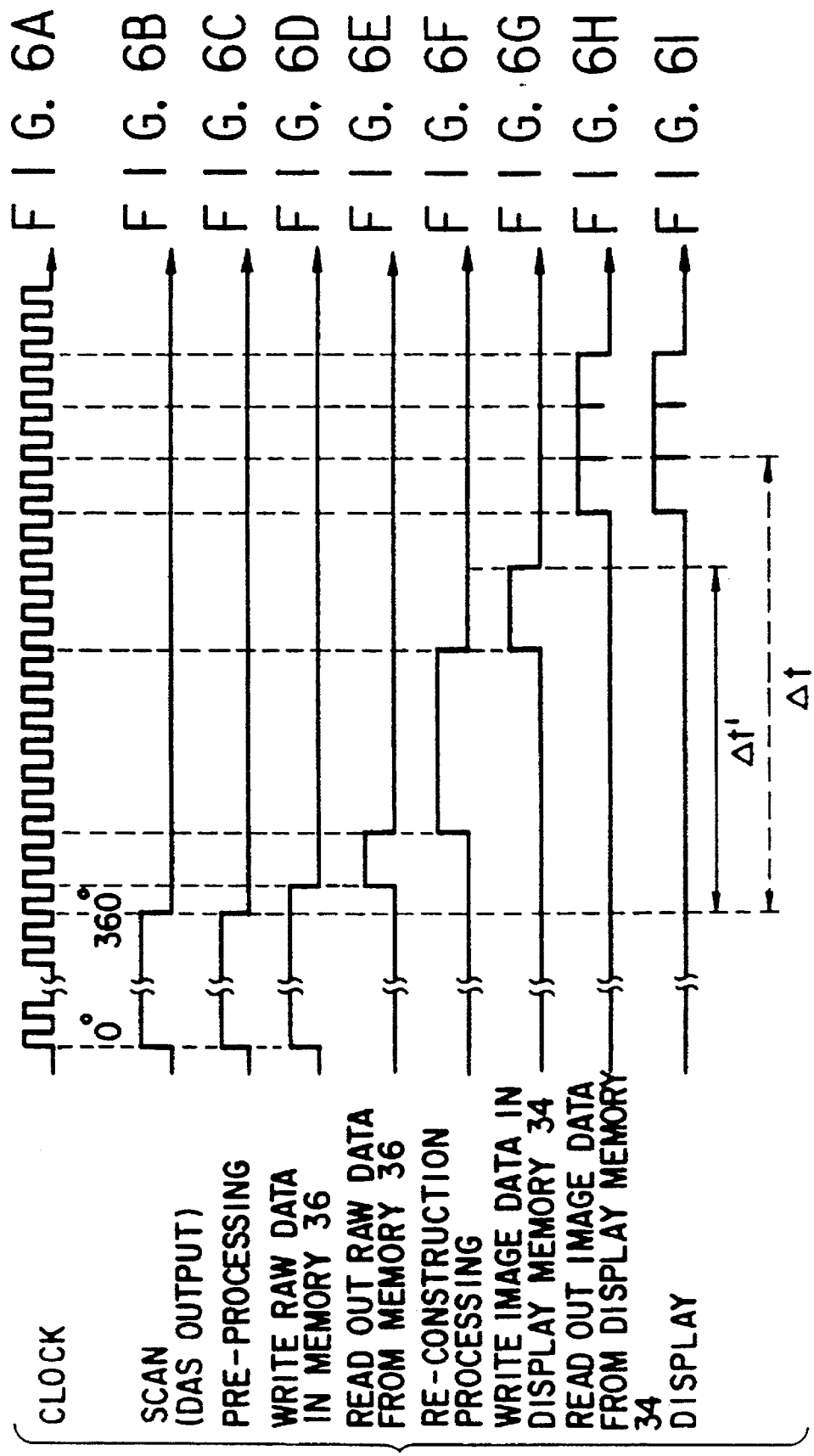

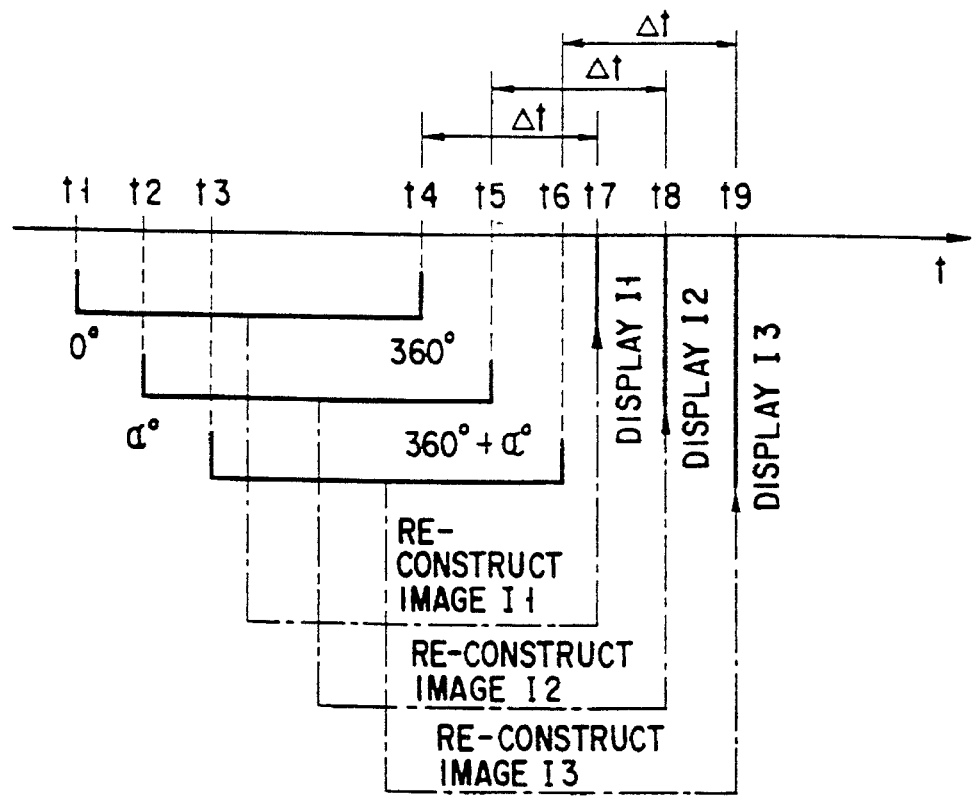
F I G. 7A
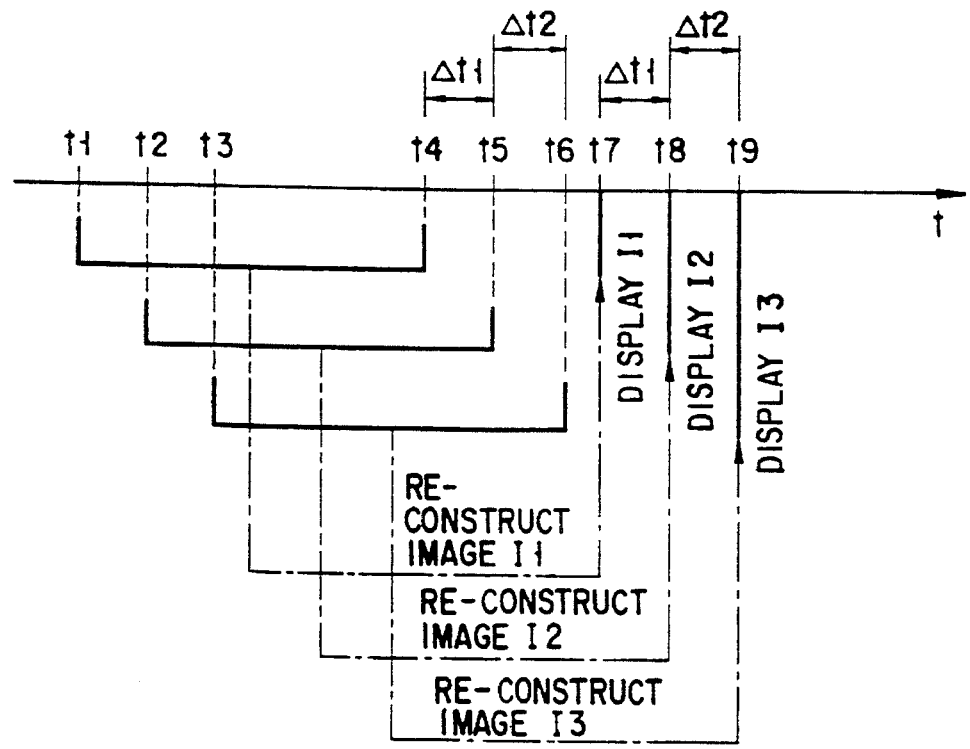
F I G. 7B

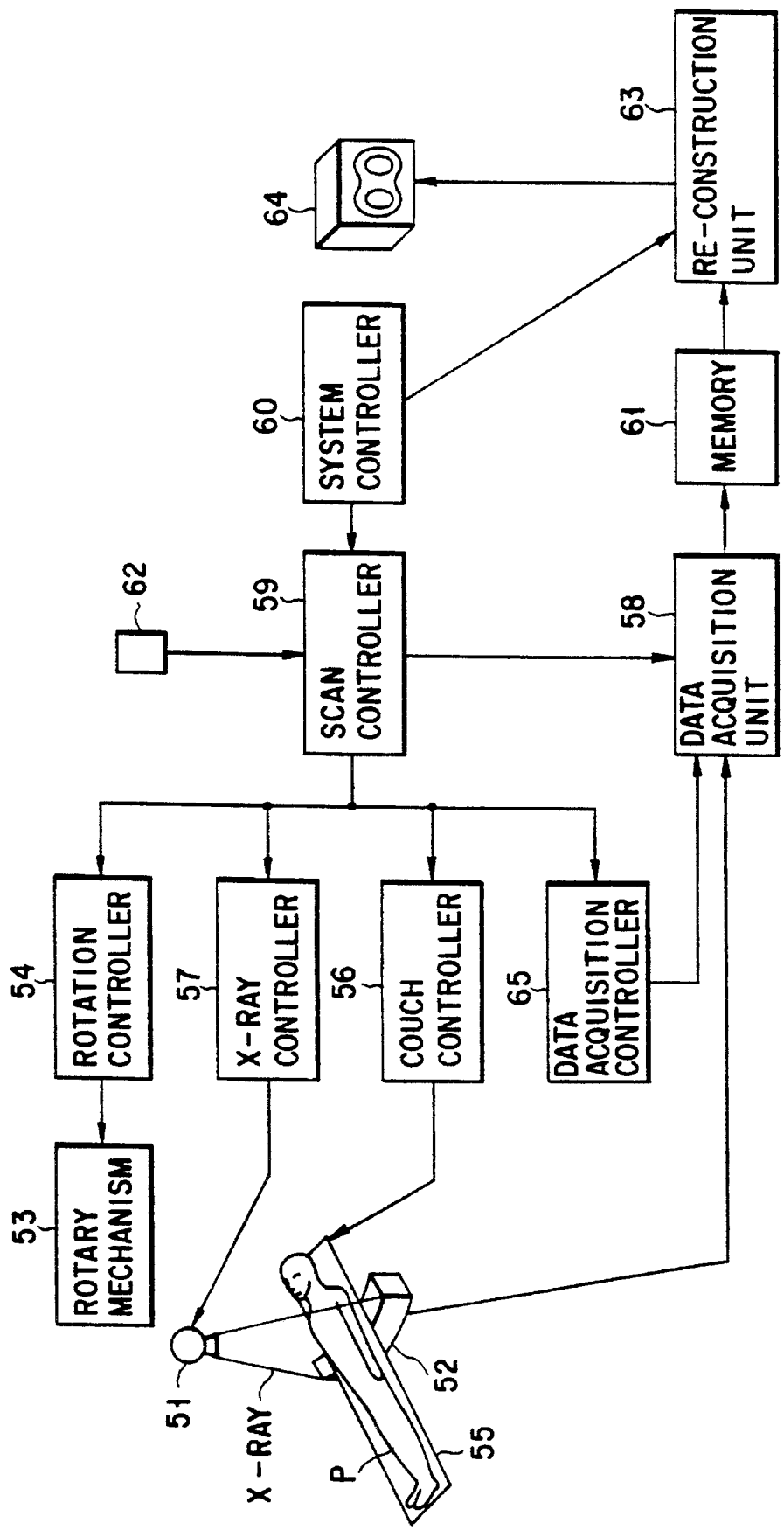
F I G. 11

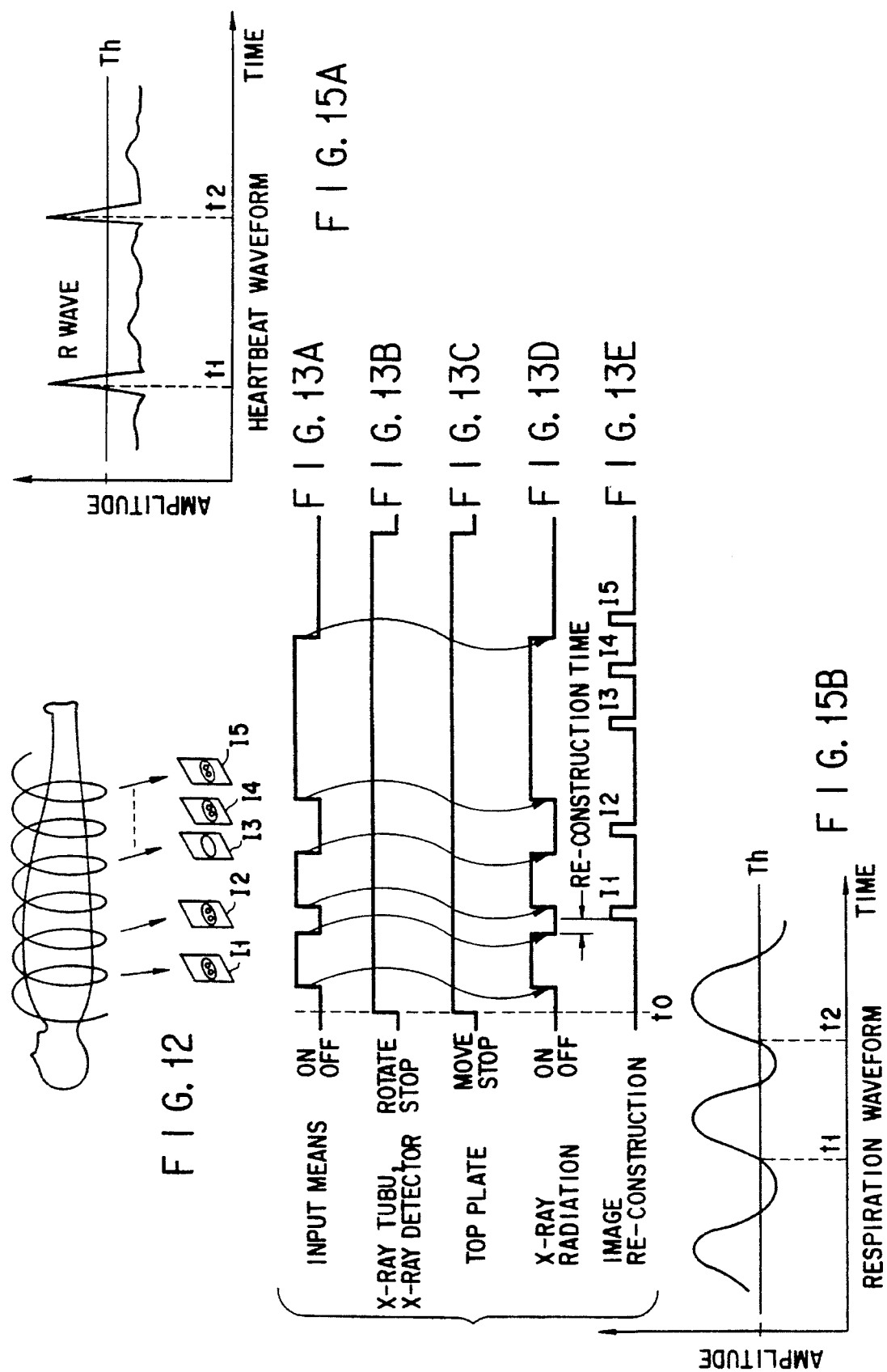

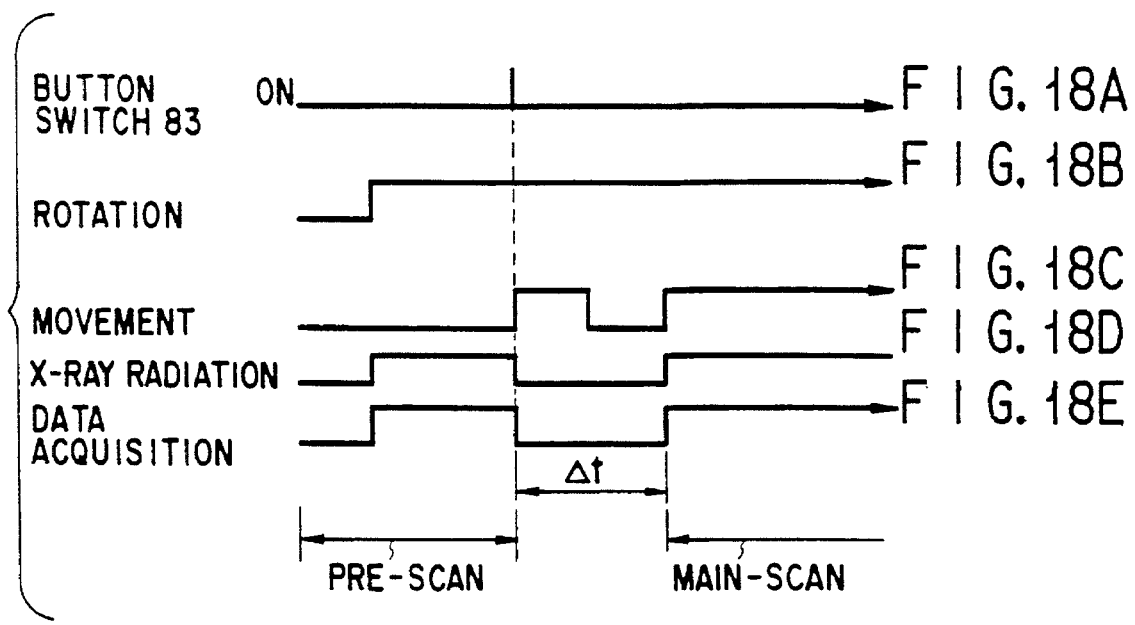
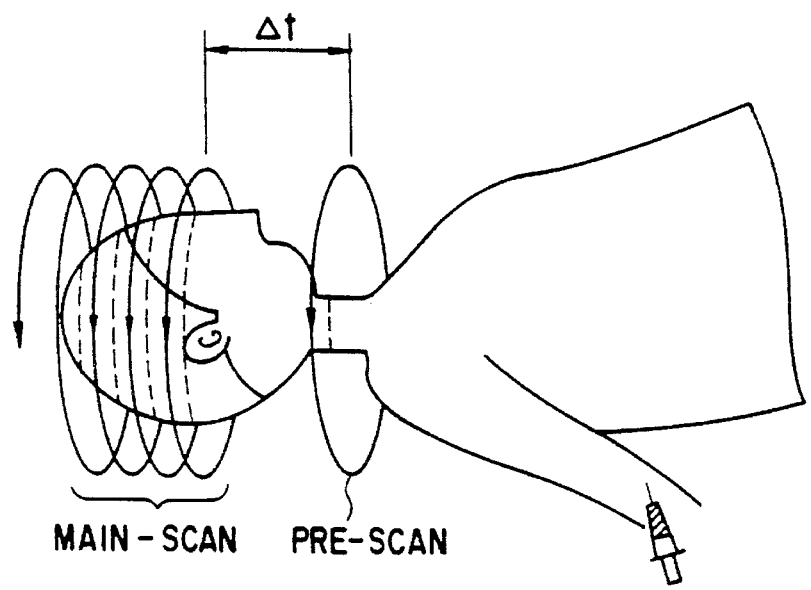
FIG. 19

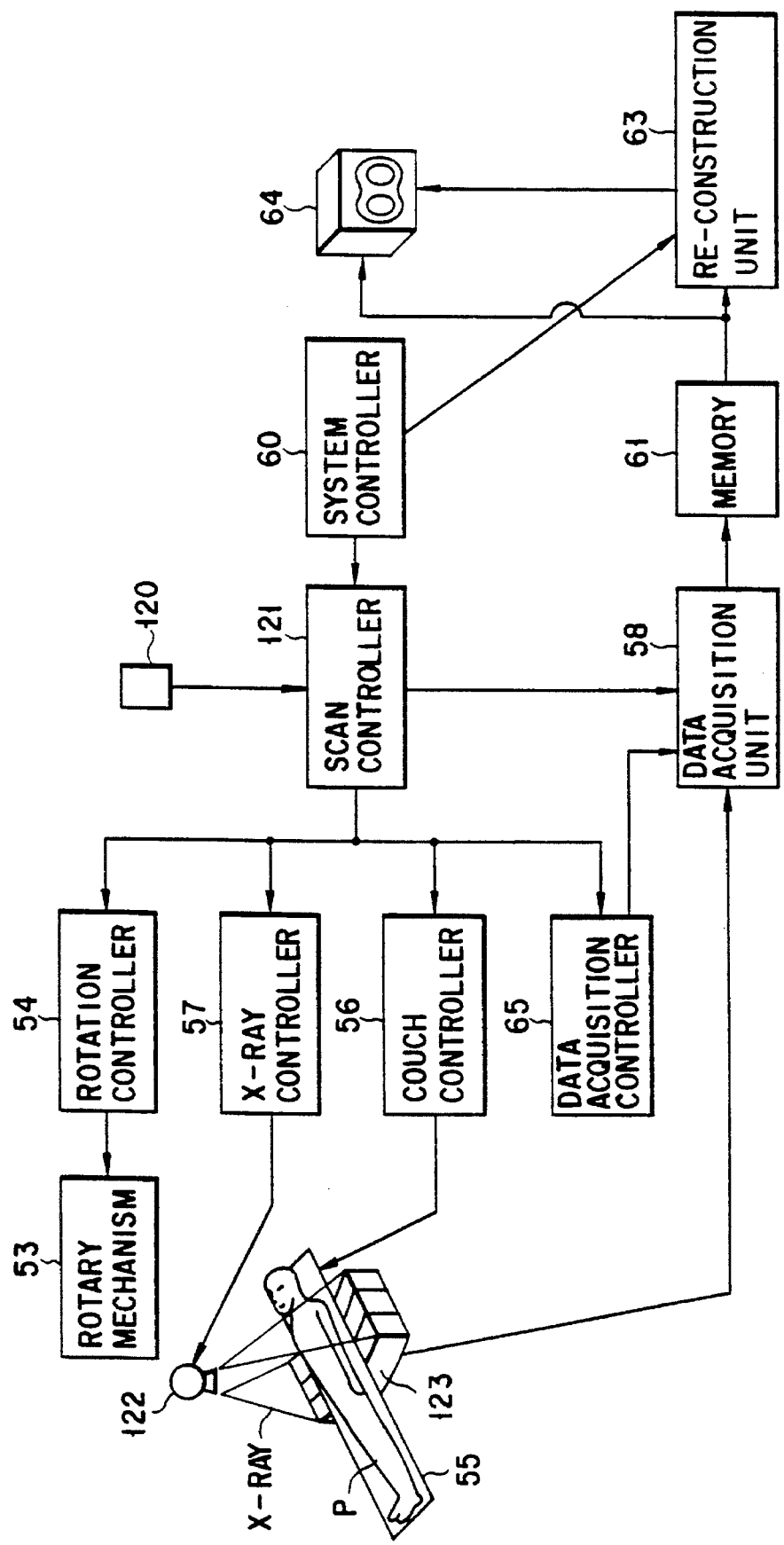
F I G. 33

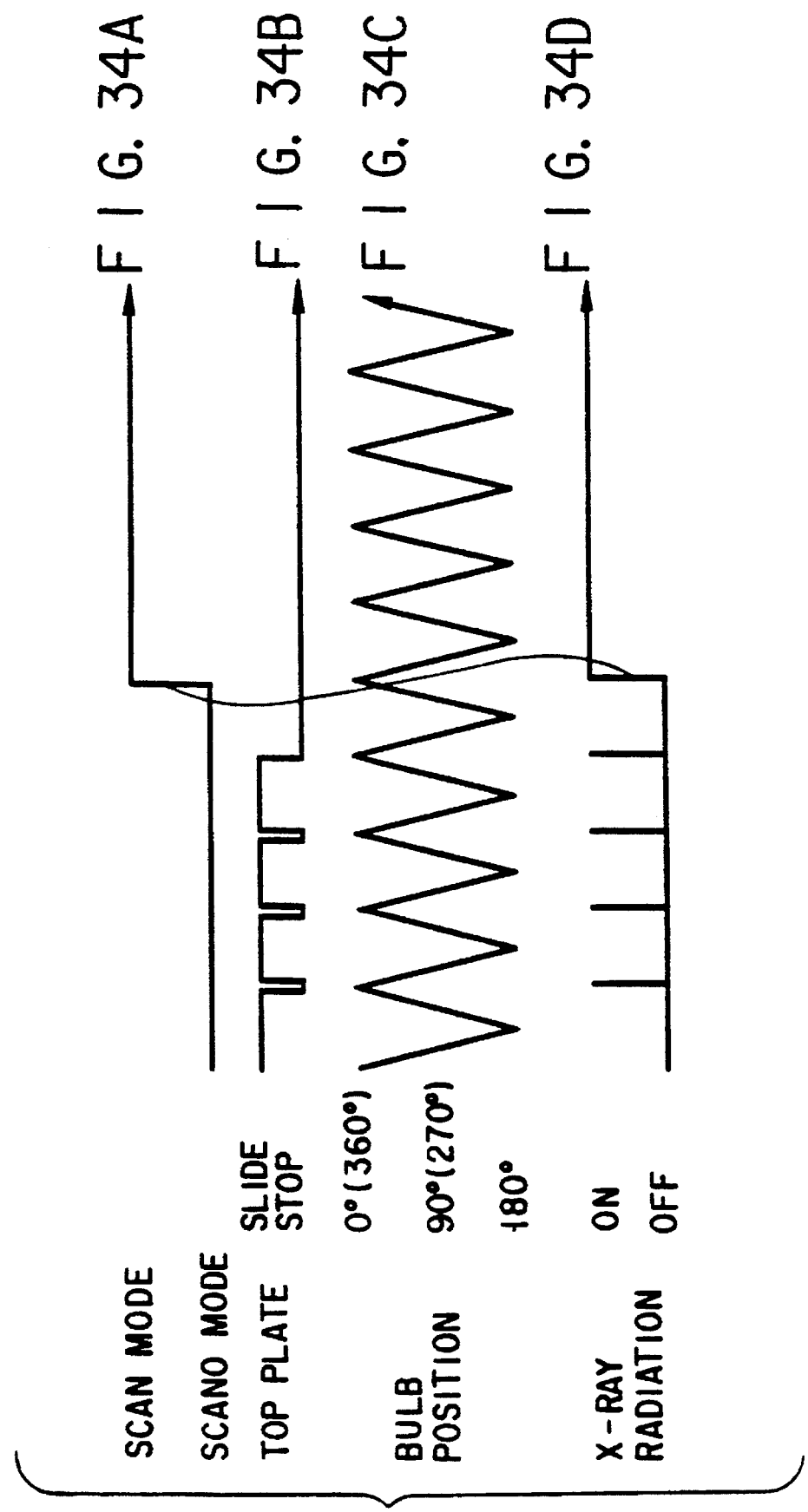

COMPUTER TOMOGRAPHY APPARATUS

This is a Division of application Ser. No. 08/347,135 filed on Nov. 23, 1994 now pending.

BACKGROUND OF THE INVENTION

1. Field of the Invention

The present invention relates to a computer tomography apparatus (to be abbreviated as a CT hereinafter) and, more particularly, to a CT which can continuously execute a scan operation.

2. Description of the Related Art

In general, in a CT, three processing operations, i.e., scan processing, image re-construction processing, and image display processing are time-serially executed. Projection data in multiple directions, which are acquired upon rotation of an X-ray tube or integral rotation of an X-ray tube and a detector array, are converted into digital data, and the digital data are subjected to pre-processing such as calibration. Thereafter, the digital data are temporarily stored as raw data in a large-capacity storage device such as a magnetic disk.

Upon execution of re-construction processing, the raw data are read out from the magnetic disk, and are supplied to a re-construction unit via a memory. Tomographic image data re-constructed by the re-construction unit are stored in the magnetic disk, and are transferred to and displayed on a CRT monitor as a video signal via a display memory.

With the advent of a slip ring, a continuous scan has become possible. With the continuous scan, a plurality of projection data in multiple directions associated with one or a plurality of slices can be time-serially acquired. These projection data in multiple directions are read out to the re-construction unit at an arbitrary timing via the magnetic disk, as described above, and are subjected to re-construction. The time required for the re-construction processing is longer than the scan time, and the magnetic disk requires long storage and access times. Therefore, it is impossible to display tomographic images in real time like cinema images while executing a continuous scan.

In recent years, high-speed re-construction processing has been examined, and is about to reach a practical application range. With this processing, tomographic images can be continuously displayed like cinema images as in an X-ray television system while executing a continuous scan. However, when this real-time X-ray CT is utilized in an actual clinical application, the following problems are posed. First, since scans are executed for an unnecessarily long period of time not only for a portion required for diagnosis but also a portion which is not required for diagnosis, the exposure amount undesirably increases. Second, since tomographic images are continuously re-constructed in a continuous scan, when a change in specific heartbeat phase over time is to be observed, an observer must select and observe the tomographic images of the specific heartbeat phase by himself or herself, and cannot concentrate on image diagnosis. Third, in the case of angiography diagnosis, since the flow-in timing of a contrast medium into a region of interest is unknown, the scan must be started sufficient before the actual flow-in. Fourth, the remaining time until an X-ray tube reaches the limit heat capacity and undergoes a forcible system-down state cannot be determined. Fifth, the scans cannot be immediately started after a scanogram used for, e.g., alignment of scans is imaged.

SUMMARY OF THE INVENTION

The present invention has been made in consideration of the above situations. It is the first object of the present invention to provide a computer tomography apparatus which can execute scans for only a required portion or for a required period of time. It is the second object of the present invention to provide a computer tomography apparatus which can display only tomographic images of a specific heartbeat phase. It is the third object of the present invention to provide a computer tomography apparatus which can automate the timing at which scans are started upon flow-in of a contrast medium into a region of interest in the case of the angiography. It is the fourth object of the present invention to provide a computer tomography apparatus which can present the remaining time until a forcible system-down state minute by minute. It is the fifth object of the present invention to provide a computer tomography apparatus which can immediately start scans after a scanogram is imaged.

A computer tomography apparatus comprising: an X-ray tube which is supported to be continuously rotatable around an object to be examined; rotation control means for controlling rotation of the X-ray tube; X-ray control means for controlling X-ray radiation from the X-ray tube; data acquisition means, arranged to face the X-ray tube to sandwich the object to be examined therebetween, for acquiring projection data on the basis of an X-ray transmitted through the object to be examined; re-construction means for re-constructing tomographic image data on the basis of the projection data acquired by the data acquisition means; display means for displaying the re-constructed tomographic image data; input means, operated by an operator, for selectively inputting an ON state and an OFF state; and control means for controlling the X-ray control means to radiate the X-ray when the ON state is selected, controlling the X-ray control means not to radiate the X-ray when the OFF state is selected, and controlling the rotation control means to continuously rotate the X-ray tube independently of the ON and OFF states.

A computer tomography apparatus comprising: an X-ray tube which is supported to be continuously rotatable around an object to be examined; rotation control means for controlling rotation of the X-ray tube; X-ray control means for controlling X-ray radiation from the X-ray tube; data acquisition means, arranged to face the X-ray tube to sandwich the object to be examined therebetween, for acquiring projection data on the basis of an X-ray transmitted through the object to be examined; re-construction means for re-constructing tomographic image data on the basis of the projection data acquired by the data acquisition means; display means for displaying the re-constructed tomographic image data; measuring means for measuring one of a heartbeat waveform signal and a respiration waveform signal of the object to be examined; and control means for controlling the rotation control means to continuously rotate the X-ray tube, and controlling the X-ray control means to radiate an X-ray in a specific phase in association with one of the heartbeat waveform signal and the respiration waveform signal.

A computer tomography apparatus which can perform an angiography, comprising: an X-ray tube which is supported to be continuously rotatable around an object to be examined; rotation control means for controlling rotation of the X-ray tube; X-ray control means for controlling X-ray radiation from the X-ray tube; data acquisition means, arranged to face the X-ray tube to sandwich the object to be examined therebetween, for acquiring projection data on the basis of an X-ray transmitted through the object to be examined; re-construction means for re-constructing tomographic image data on the basis of the projection data acquired by the data acquisition means; display means for displaying the re-constructed tomographic image data; and control means for controlling the rotation control means, the X-ray control means, the data acquisition means, and couch control means to execute a pre-scan at a first scan position, and controlling the rotation control means, the X-ray control means, the data acquisition means, and the couch control means to execute a main scan at a second scan position at a downstream of the first scan position, in which the control means starts the main scan after an elapse of a time required for a blood flow to reach the second scan position from the first scan position after the end of the pre-scan.

A computer tomography apparatus comprising: an X-ray tube which is supported to be continuously rotatable around an object to be examined; rotation control means for controlling rotation of the X-ray tube; X-ray control means for controlling X-ray radiation from the X-ray tube; data acquisition means, arranged to face the X-ray tube to sandwich the object to be examined therebetween, for acquiring projection data on the basis of an X-ray transmitted through the object to be examined; re-construction means for re-constructing tomographic image data on the basis of the projection data acquired by the data acquisition means; remaining time calculation means for calculating a remaining time until the X-ray tube reaches a limit heat capacity when X-ray radiation is continued with a current X-ray energy; and display means for displaying the remaining time and the tomographic image data.

A computer tomography apparatus comprising: an X-ray tube which is supported to be continuously rotatable around an object to be examined, and radiates a cone-shaped X-ray beam; rotation control means for controlling rotation of the X-ray tube; X-ray control means for controlling X-ray radiation from the X-ray tube; a two-dimensional detector array constituted by arraying a plurality of acquisition elements which are arranged to face the X-ray tube to sandwich the object to be examined therebetween, and acquire projection data on the basis of an X-ray transmitted through the object to be examined; re-construction means for re-constructing tomographic image data on the basis of the projection data acquired by the two-dimensional detector array; display means for displaying the tomographic image data; and control means for executing a first mode for imaging a scanogram and a second mode for executing a scan in turn, for controlling the rotation control means to rotate the X-ray tube and controlling the X-ray control means to radiate the X-ray when the X-ray tube is at a specific angle in the first mode, for controlling the rotation control means to rotate the X-ray tube and controlling the X-ray control means to continuously radiate the X-ray in the second mode, and for controlling the rotation control means to continue rotation of the X-ray tube even while an operation mode is switched from the first mode to the second mode.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 is a flow chart showing an operation in a fluoroscopy mode of the first embodiment;

FIG. 5 is a chart showing the timings of scan, pre-processing, re-construction, and display operations in a CT fluoroscopy;

FIG. 6 is a chart showing the operation sequence from data acquisition to display in association with a single tomographic image;

FIGS. 7A and 7B are charts showing the data acquisition and display timings of a plurality of tomographic images acquired by a continuous scan;

FIG. 11 is a block diagram showing the arrangement of the second embodiment;

FIG. 12 is a view showing the path of an X-ray tube during a helical scan;

FIG. 13 is a timing chart showing the operation of the second embodiment;

FIGS. 15A and 15B are graphs showing the waveforms of vital phenomena;

FIG. 18 is a timing chart showing the operation of the fourth embodiment;

FIG. 19 is a view showing the scan positions of a pre-scan and a main scan;

FIG. 33 is a block diagram showing the arrangement of the sixth embodiment; and

FIG. 34 is a timing chart showing the operation of the sixth embodiment.

DETAILED DESCRIPTION OF THE PREFERRED EMBODIMENTS

The preferred embodiments of a computer tomography apparatus (CT) according to the present invention will be described hereinafter with reference to the accompanying drawings.

First Embodiment

Figure 2:
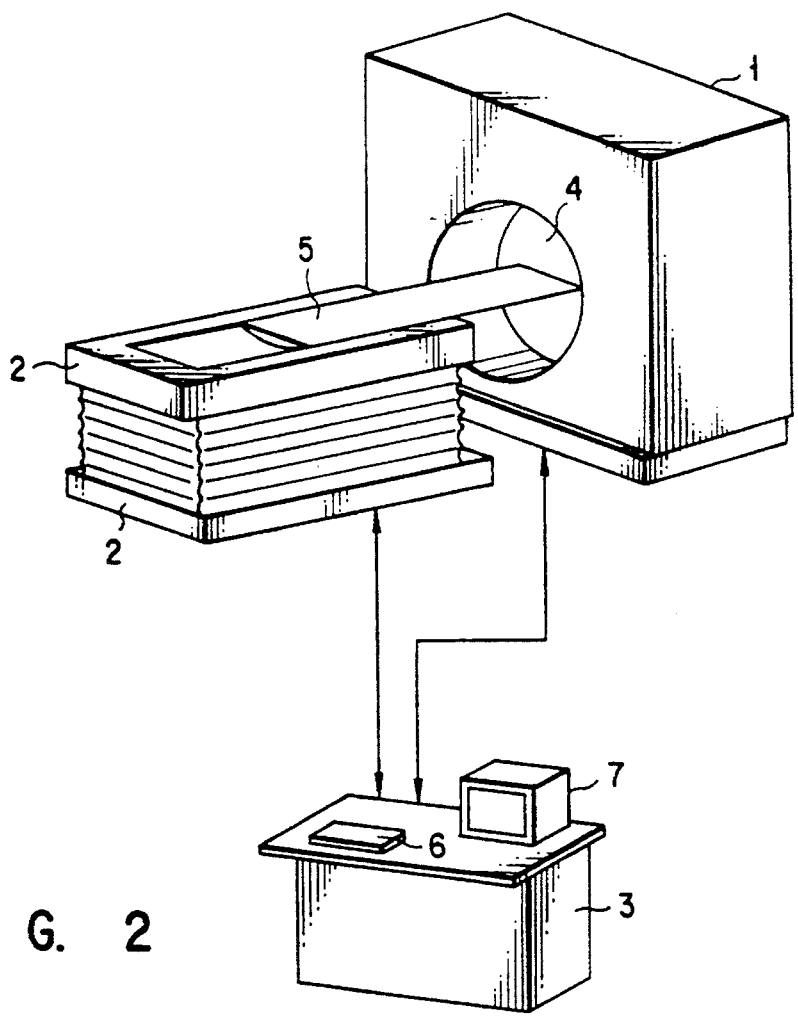
FIG. 2 is a perspective view showing the outer appearance of a computer tomography apparatus.

FIG. 2 is a schematic perspective view showing the arrangement of the first embodiment. A CT of this embodiment is constituted by a frame 1, a couch 2, and an operation console 3. The frame 1 has an opening portion 4, through which an object to be examined is inserted, at its central portion. The couch 1 is arranged in front of the frame 1. The height of the couch 2 can be electromotively adjusted. A top plate 5 on which an object to be examined is placed is arranged on the upper surface of the couch 2, and is electromotively slidable from the upper surface of the couch 2 toward the frame 1. Although not shown, casters and the like are attached to the lower portion of the frame 1, and the frame 1 is manually slidable toward the couch 2. Since the CT fluoroscopy is sometimes used during a surgical operation, it is preferable in terms of safety in this case to change the slice position by moving the frame 1 in place of moving the top plate 5. In a tomography mode, it is a general practice to change the slice position by sliding only the top plate 5.

A keyboard (which may include a mouse) 6 and a CRT monitor 7 are arranged on the operation console 3, and the operation console 3 houses a control unit. The control unit is connected to both the frame 1 and the couch 2.

Figure 3:
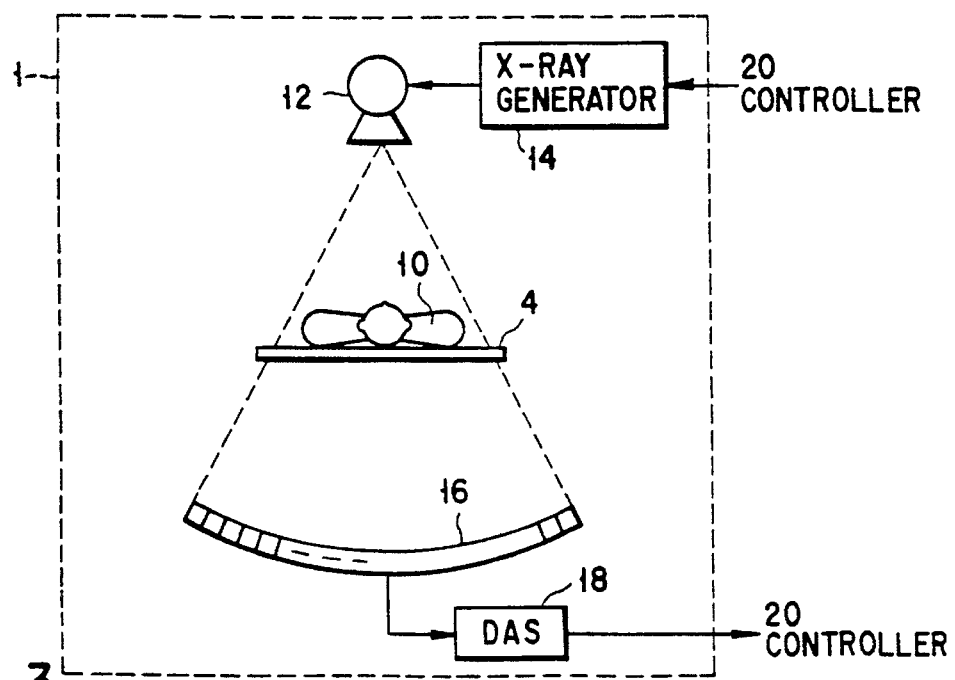
FIG. 3 is a view showing the structure inside a frame shown in FIG. 2.

In the frame 1, as shown in FIG. 3, an X-ray tube 12 for irradiating fan-shaped X-ray beam radiation onto an object 10 to be examined placed on the top plate 5, and a detector array 16, which is constituted by a plurality of detectors arranged in an arc shape to have the focal point of the X-ray tube 12 as the center, and detects X-rays transmitted through the object 10 to be examined in multi channels, are supported by a rotary unit. The X-ray tube 12 and the detector array 16 can be integrally and continuously rotated around the object 10 to be examined while facing each other to sandwich the object 10 to be examined therebetween. In addition, the X-ray tube 12 and the detector array 16 are electrically connected to a stationary unit via a slip ring. With this structure, projection data in multiple directions associated with the object 10 to be examined required for re-constructing a single tomographic image can be continuously acquired while the X-ray tube 12 and the detector array 16 are continuously rotated around the object 10 to be examined. When the X-ray tube 12 and the detector array 16 are continuously rotated at an identical slice position, a so-called dynamic scan for tracing a change in tomographic image upon flow-in and flow-out of a contrast medium is allowed; when the slice position is changed in synchronism with the rotation, a so-called helical scan is allowed. Note that the CT of this type is called the third generation (R/R system). Note that the frame 1 is not limited to this type, and may be a so-called fourth generation (R/S system) in which detectors are arranged around an object to be examined throughout 360°, and only the X-ray tube 12 is rotated, or may be a so-called fifth generation (S/S system) in which the X-ray tube 12 is arranged around an object to be examined throughout 360° in addition to the detectors.

An X-ray generator 14 for supplying a continuous or pulsed tube current and tube voltage to the X-ray tube 12 to generate X-rays is arranged on the stationary unit of the frame 1, and is connected to the X-ray tube 12 via a slip ring. Also, a data acquisition system (DAS) 18 is arranged on the stationary unit of the frame 1, and is connected to the detector array 16 via the slip ring. The DAS 18 comprises an integrator for temporally integrating output signals from the detectors of the detector array 16, a multiplexer for serially fetching the output from the integrator at a high speed in units of channels, an analog-to-digital converter for converting an output signal from the multiplexer into a digital signal, and the like. The DAS 18 acquires projection data which reflect the X-ray transmittances in units of X-ray paths, and outputs the acquired data.

Figure 4:
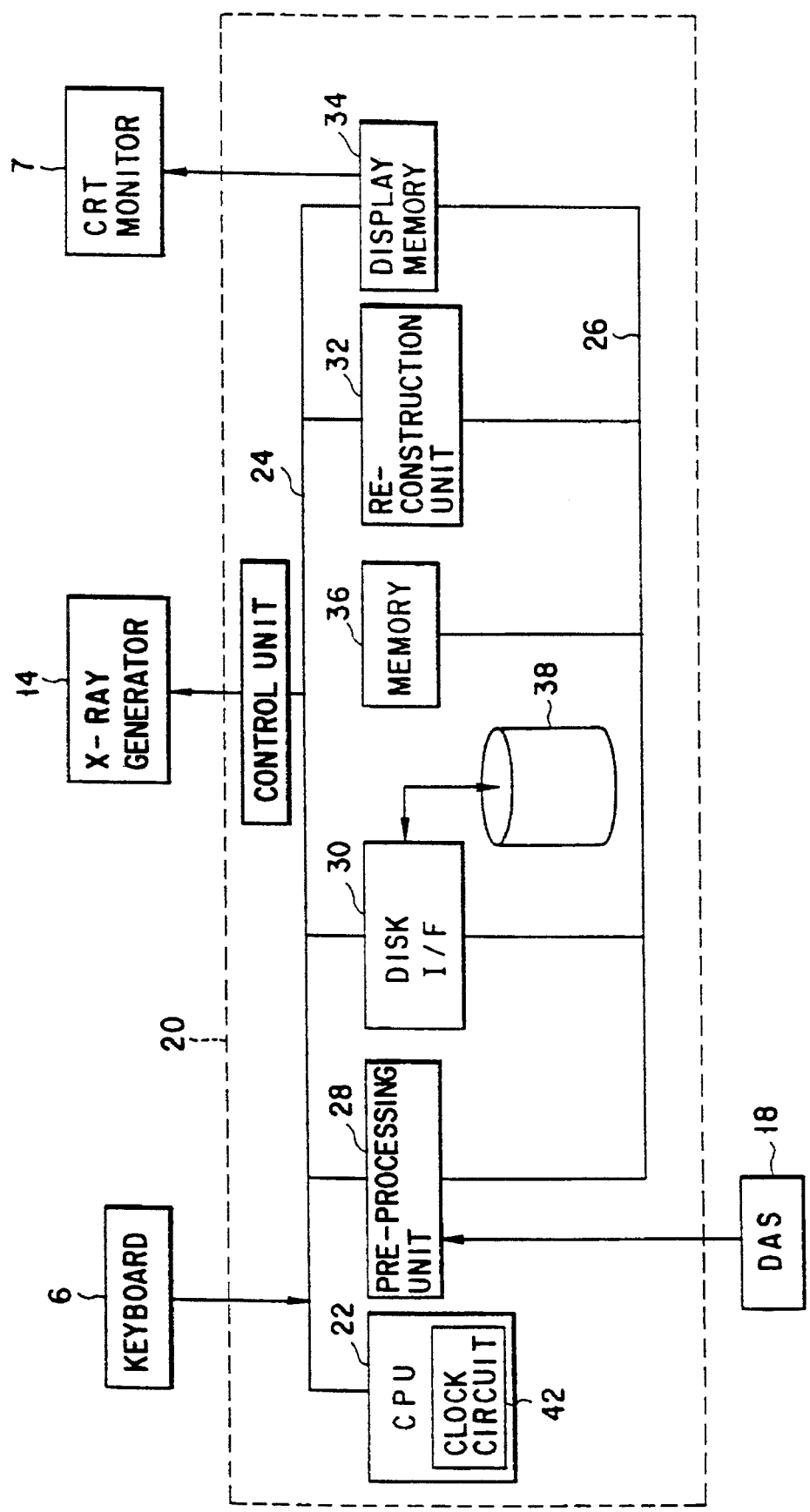
FIG. 4 is a block diagram of a control unit.

FIG. 4 is a block diagram of a control unit 20 in the operation console 3. A CPU 22 as a host controller is arranged, and a control bus 24 and a data bus 26 are connected to the CPU 22. The CPU 22 incorporates a clock circuit 42 to manage the operations and times of the respective units using clocks from the clock circuit 42 and to supply the clocks to the respective units in the control unit 20 as common clocks. The control bus 24 is connected to a pre-processing unit 28, a disk interface (disk I/F) 30, a re-construction unit 32, and a display memory 34. The control bus 24 is also connected to the above-mentioned keyboard 6 and X-ray generator 14. The data bus 26 is connected to the pre-processing unit 28, the disk I/F 30, the re-construction unit 32, the display memory 34, and a memory 36. The disk I/F 30 is connected to a magnetic disk device 38 as a large-capacity storage unit. The data bus 26 is also connected to the DAS 18. Projection data from the DAS 18 are subjected to pre-processing such as calibration in the pre-processing unit 28, and thereafter, are temporarily written as raw data in the memory 36 comprising, e.g., a rewritable DRAM via the data bus 26. Furthermore, the projection data are read out from the memory 36, and are supplied to the re-construction unit 32. The re-construction unit 32 re-constructs tomographic image data on the basis of projection data in multiple directions. The tomographic image data is temporarily written in the display memory 34 comprising, e.g., a rewritable DRAM, and is read out therefrom to the CRT monitor 7 to be displayed as a tomographic image. The tomographic image data is read out from the display memory 34, and is stored in the magnetic disk device 38 via the disk I/F 30.

The operation of this embodiment will be described below. FIG. 1 is a flow chart of a fluoroscopy mode. FIG. 5 is a chart showing the schematic flow from the scan to display in the fluoroscopy mode. This embodiment has a fluoroscopy mode and a tomography mode as operation modes, as described above, and one of these modes is selectively set in accordance with an operator's instruction input via the keyboard 6.

When the operation is started, the continuous rotation of the X-ray tube 12 and the detector array 16 is started in step #10 to start a continuous scan. The continuous scan is defined by continuously repeating a scan operation. The scan operation is defined by acquiring projection data in multiple directions required for re-constructing a single tomographic image while rotating the X-ray tube 12 and the detector array 16. During the continuous scan, the slice position may be fixed or changed. As will be described later, according to this embodiment, data acquisition, image re-construction, and display operations are executed at a high speed as a series of operations, and the time interval (time difference) from the scan operation time for acquiring projection data for one image until the display of a tomographic image via the re-construction processing is constant for all the scan operations. For these reasons, the time interval from the scan operation to the display of a tomographic image does not disturb real-time reproduction of an actual motion of the object 10 to be examined since it does not become irregular due to the presence/absence of wait times upon read/write accesses of the memories 34 and 36. Therefore, tomographic images can be displayed in almost real time like cinema images. The fluoroscopy mode is used, for example, when the arrival of the distal end of a trocar to a tumor portion during the centesis is confirmed by continuously displaying tomographic images while performing a continuous scan. In this case, the slice position is fixed during the continuous scan. This mode can also be used for aligning the slice position for a normal tomography. In this case, it is required to freely change the slice position. The slice position may be changed by sliding the top plate 5. However, when the fluoroscopy mode is used during a surgical operation, it is not preferable to move a patient to whom various tubes and devices are attached. For this reason, it is desirable to change the slice position by sliding the frame 1. In this case, it is preferable that the frame 1 comprise a power assist mechanism, so that a doctor can easily manually move the frame 1. Furthermore, the slice position need not be changed at a constant speed in the fluoroscopy mode unlike in a normal helical scan, and the stop and movement may be irregularly repeated or the moving speed may be changed.

Projection data which are acquired by and output from the DAS 18 during the scan operation are subjected to pre-processing such as calibration in the pre-processing unit 28, and thereafter, are sequentially written in the memory 36 as raw data. For example, the rotational speed of the X-ray tube 12 and the detector array 16 is assumed to be 1 second per revolution, and a single continuous scan period is determined to be a period (50 sec) required for 50 revolutions of the X-ray tube 12 and the detector array 16. This period is set not to exceed an allowable time which is determined in consideration of the heat resistance of the X-ray tube 12 and safety of the object 10 to be examined against exposure. The memory 36 has a storage capacity of about 100 MB under the assumption that 2-MB raw data are acquired during one revolution, so that all raw data for a single continuous scan can be stored. The display memory 34 has a storage capacity capable of storing a plurality of tomographic image data acquired by the single continuous scan.

In step #12, the CPU 22 checks if raw data required for re-constructing single tomographic image data are acquired. If Y (YES) in step #12, the acquired raw data are transferred from the memory 36 to the re-construction unit 32 in step #14. Note that the scan operation is continuously executed. Since the raw data is transferred from the DAS 18 to the re-construction unit 32 via the memory 36, the time required from the scan operation until the start of the re-construction processing can be remarkably shortened as compared to a case wherein data are transferred via a magnetic disk which requires a long access time. In the conventional apparatus, all raw data are temporarily stored in a magnetic disk, and are read out and re-constructed during an idle time. For this reason, a long period of time is required from the scan operation to the start of the re-construction processing, and real-time processing cannot be realized.

The processing time of the re-construction unit 32 is shorter than that required for the scan operation (data acquisition time), i.e., high-speed processing is adopted. With this processing, a temporal shift of the end of re-construction of a tomographic image from the scan operation, i.e., the time difference from the end of acquisition of projection data required for re-constructing a single tomographic image to the end of re-construction of the acquired data, can be prevented from being accumulated every time a scan operation is repeated. The re-construction unit 32 is constituted by a plurality of processors connected in parallel with each other, and in the high-speed processing, the processors parallelly execute re-construction processing by dividing raw data in units of views or channels (normally, one detector corresponds to one channel). By increasing the number of parallel processing operations, the processing speed can be increased. Also, by increasing the clock speed, the processing speed can be increased.

In order to realize the high-speed re-construction processing, the number of views per 360° (one revolution) is decreased (thinned out or combined). For example, in a normal tomography mode, projection data are required at a rate of 900 views per revolution, i.e., the DAS 18 repeats data acquisition 900 cycles during one revolution. On the other hand, in the fluoroscopy mode, data acquisition is repeated at a rate of 450 views per revolution with this operation, the spatial resolution of a tomographic image is lowered. However, the objective of the fluoroscopy mode by the continuous scan is to instantly observe the movement of the object 10 to be examined in almost real time. Since a tomographic image with a high spatial resolution can be imaged in the tomography mode, a decrease in spatial resolution does not pose any practical problem. In order to further shorten the re-construction time, the number of pixels upon re-construction may be decreased. In the normal tomography mode, a single tomographic image is re-constructed to have a size of 512×512 pixels, and is displayed in this size. On the other hand, in the fluoroscopy mode, a single tomographic image is re-constructed to have a size of 256×256 pixels. When the re-constructed image is displayed, the pixels are interpolated to increase the number of pixels to 512×512 (pixels), thereby shortening the re-construction time.

Furthermore, a tomographic image is repetitively re-constructed during the continuous scan in this case, if a single tomographic image is re-constructed during one revolution, the next tomographic image is re-constructed during the next revolution, and the rotational speed of the X-ray tube 12 and the detector array 16 is 1 sec per revolution, tomographic images are re-constructed at a rate of one image per second. In this embodiment, in order to improve this re-construction rate, a technique which has already been described in Jpn. Pat. Appln. KOKAI Publication No. 4-266744 may be adopted. In this technique, each time the X-ray tube 12 and the detector array 16 are rotated through a small angle α° (e.g., α°=10°), a partial image is sequentially re-constructed from projection data for 10°. By adding 36 partial images for 360°, a single complete tomographic image for 360° is generated. Once a single tomographic image is generated, the latest partial image is added to this tomographic image, the oldest partial image is subtracted from the tomographic image, and this operation is repeated. With this operation, each time the X-ray tube 12 and the detector array 16 are rotated through 10°, a new tomographic image is sequentially generated, and a tomographic image can be continuously acquired at a high re-construction rate. In order to improve the re-construction rate, a technique described in Japanese Patent Application KOKOKU Publication No. 1-23136 may be adopted. In this technique, re-construction image information is obtained from a group of projection data for one image by back projection. The latest projection data acquired immediately after the group of projection data, and difference data between the latest projection data and positionally corresponding projection data in the group are back-projected to the re-construction image information. With this operation, temporally shifted next re-construction image information can be generated at high speed. Both these techniques are based on the principle that a re-constructed tomographic image is sequentially updated, and the re-construction rate may be improved by adopting other techniques based on this principle.

Upon completion of re-construction, tomographic image data is written in the display memory 34 in step #16. The current tomographic image data is repetitively read out at a predetermined period and is transferred to the CRT monitor 7, so that the current tomographic image is displayed on the CRT monitor 7 in a freeze state until the next tomographic image is re-constructed and displayed. Such a display method is the same as the cinema display method in an X-ray imaging apparatus. When the next tomographic image is written during the read access of the display memory 34, different pieces of information are read out for the upper and lower portions of an image. For this reason, the write access must be waited during the read access.

In step #18, the CPU 22 checks if a single continuous scan is completed, i.e., 50 seconds have elapsed from the beginning of the scan. If N (NO) in step #18, the flow returns to step #12, and the control waits for the end of acquisition of data required for re-constructing the next tomographic image. However, if Y in step #18, raw data in the memory 36 are stored in the magnetic disk device 38 in step #20. If raw data need not be stored, step #20 may be omitted. It is checked in step #22 if the next continuous scan is performed. If Y in step #22, the flow returns to step #10; otherwise, the flow ends.

Note that raw data for at least the last continuous scan are stored in the memory 36. Therefore, when a tomographic image is to be displayed again after the end of the continuous scan, raw data read out from the memory 36 can be re-constructed. As described above, since the tomographic image can be observed in almost real time in the fluoroscopy mode, the image is often used as an image for assisting a surgical operation during the operation such as a centesis. In such a case, since an operator (doctor) cannot often observe a monitor during the operation, an assistant gives various instructions to the operator while observing the monitor. However, the doctor may often require to see the progress of the centesis upon completion of a single continuous scan. In order to meet such a requirement, the last tomographic image is frozen after the end of the continuous scan. Upon request by the doctor, raw data read out from the memory 36 are re-constructed and the re-constructed image is displayed frame by frame, thus allowing the doctor to see the image.

The operation from data acquisition to display of single tomographic image data will be described in detail below. FIG. 6 is a timing chart showing this operation. While the X-ray tube 12 and the detector array 16 are rotated around the object 10 to be examined, projection data are output from the DAS 18 for each small angle. The projection data are sequentially written in the memory 36 as raw data via the pre-processing unit 28. After all projection data for all the angular components (0° to 360°) required for re-constructing a single tomographic image, the projection data are read out from the memory 36 and are transferred to the re-construction unit 32. In the re-construction unit 32, tomographic image data is re-constructed at high speed, i.e., in a shorter period of time than the data acquisition time, and is written in the display memory 34. During this interval, an access to the magnetic disk device 38 is inhibited. The tomographic image data is read out from the display memory 34, and is supplied to the CRT monitor 7 to be displayed thereon. As described above, the read access of the tomographic image data from the display memory 34 is repeated until the next tomographic image is displayed.

Figure 8:
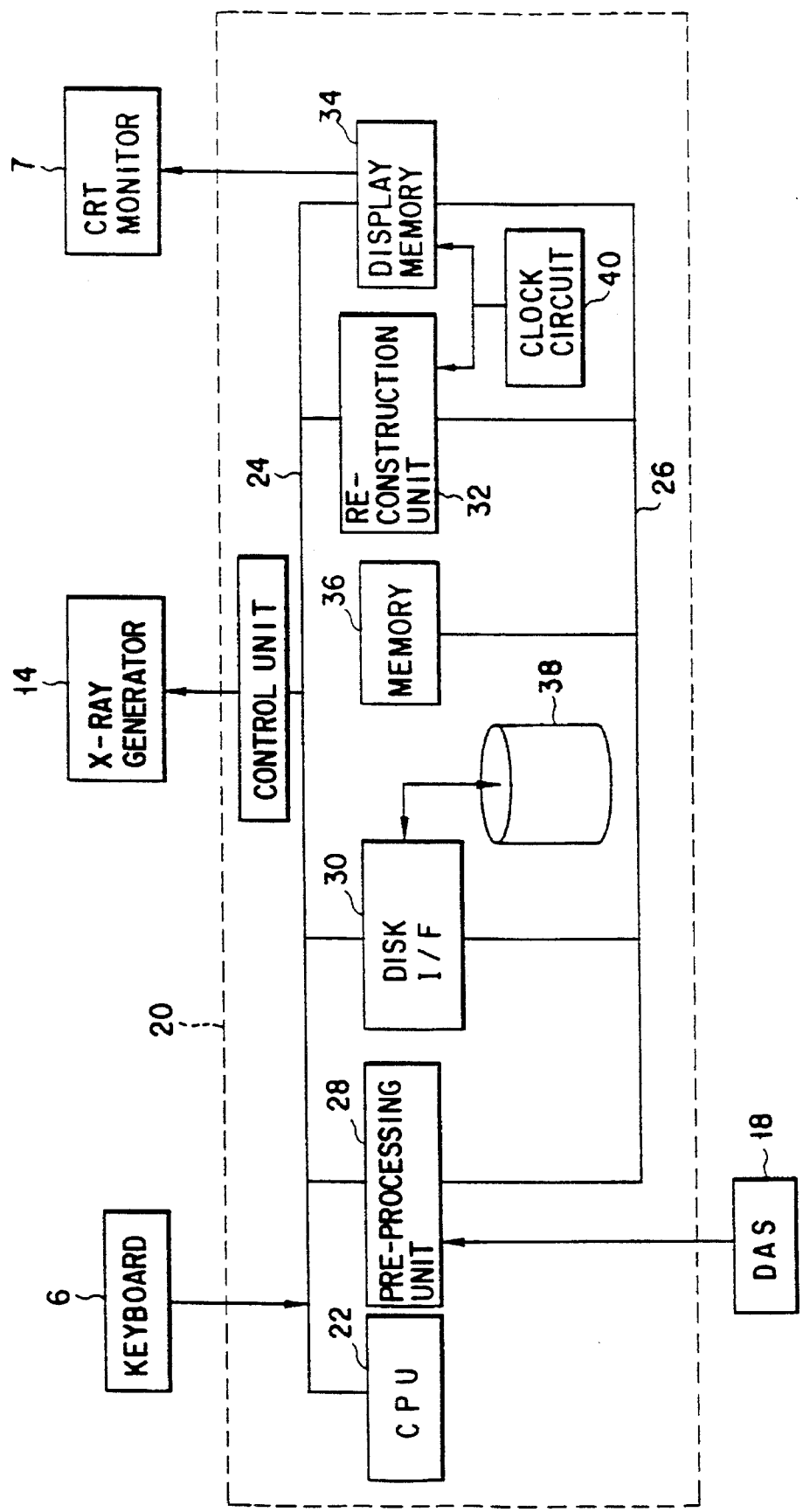
FIG. 8 is a block diagram showing a modification of FIG. 4.

It is important for real-time cinema display to faithfully reproduce the speed of a movement in addition to shortening of the time from the scan operation to the display of a tomographic image. For example, when two tomographic images which are acquired at a 1-sec interval are switched and displayed at a 1.1-sec interval, an actual movement is not reproduced. In this embodiment, as shown in FIG. 7A, a time difference $\Delta t$ from the end of the scan operation for one tomographic image (end of data acquisition) to the beginning of the display of the tomographic image is set to be constant for all tomographic images I1, I2, I3, . . . . In other words, tomographic images I1 and I2 are displayed at an interval equal to the interval $\Delta t1$ between their scan operations, tomographic images I2 and I3 are displayed at an interval equal to the interval $\Delta t2$ between their scan operations, and thereafter, tomographic images are similarly sequentially switched and displayed to have a time difference equal to the scan operation interval. Therefore, the time scales of the scan operations and the display operations are equalized, thus realizing faithful reproduction of an actual movement. In general, a time period $\Delta t'$ from the scan operation to the end of a write access of tomographic image in the display memory 34 varies depending on the state of the load on the CPU 22, e.g., is prolonged during the scan and is shortened in a non-scan period. Therefore, when a read access is started immediately after a write access of tomographic image data in the display memory 34 is completed, an actual movement cannot be reproduced. In this embodiment, the time difference from the scan operation to the beginning of the read access of tomographic image data (the beginning of the display) is fixed to be at least equal to or longer than a time (maximum time) required when the CPU 22 has a maximum load, thereby realizing reproduction of an actual motion. This time control can be realized by a known technique. As shown in FIG. 4, the operations of the units 28, 32, 34, and 36 may be systematically controlled by the CPU 22, or as shown in FIG. 8, common clocks may be used for the re-construction unit 32 and the display memory 34. In addition, although not shown, timer circuits may be arranged in the pre-processing unit 28 and the display memory 34, the pre-processing unit 28 may inform the end time of arrival of projection data for one image to a controller in the display memory 34, and tomographic image data may be read out from the display memory 34 after an elapse of a predetermined period of time from the informed time.

As described above, according to this embodiment, the movement of an object can be observed in almost real time like cinema images while executing a continuous scan. Therefore, the blood flow (the flow of a contrast medium) can be observed, a tomography operation can be executed at an optimal timing in the fluoroscopy mode, and an aid to a biopsy or the like can be realized by observing the movement of a catheter or a change in blood flow.

As a modification for increasing the data acquisition speed, an X-ray tube having multi tube bulbs (e.g., three tube bulbs) may be used or the rotational speed of the X-ray tube may be increased in the case of the third generation CT apparatus, or the fifth generation CT apparatus may be used. In the fifth generation CT apparatus, high-speed rotation is realized by arranging a large number of X-ray tubes around an object to be examined, or by scanning an electron beam using a bell-shaped X-ray tube having a ring-shaped cathode surrounding an object to be examined.

As a modification for increasing the data acquisition speed and shortening the re-construction time, a so-called half-scan re-construction system for performing re-construction based on projection data for, e.g., 180° smaller than 360° may be adopted in place of re-construction performed based on projection data for 360°.

As a modification for preventing an increase in exposure amount upon execution of the continuous scan, an X-ray generator which can generate X-rays by a low tube current or an X-ray generator which can generate pulse X-rays may be adopted. The X-ray dose largely depends on mAs as the product of a tube current mA and an exposure time t (seconds). For this reason, in order to decrease the dose, the tube current must be decreased. However, since a normal CT apparatus is designed to output X-rays by a tube current of several hundreds of mA, the control method of a tube voltage and tube current is changed to be able to output X-rays by a tube current as low as several tens of mA.

Figure 9:
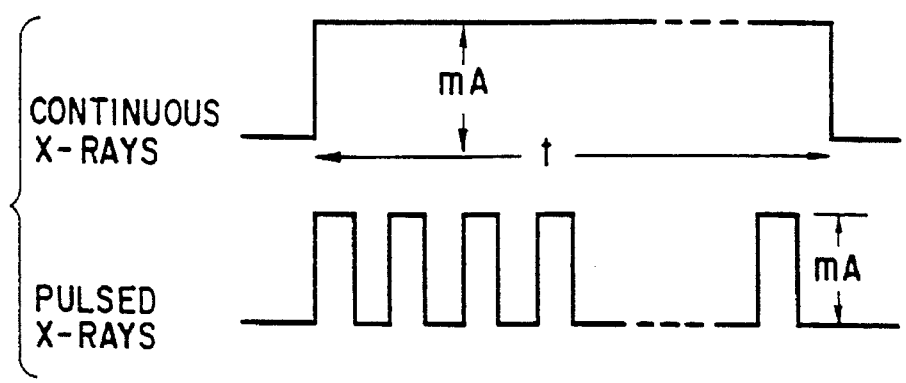
FIG. 9 is a chart showing a pulse X-ray used for decreasing the exposure amount.

Also, in order to decrease the exposure amount, a method using a pulse X-ray in place of a continuous X-ray which is popularly used in CT apparatuses may be used. For example, as shown in FIG. 9, when a pulse X-ray having a duty ratio of 50% (i.e., an X-ray is radiated for a time half the total time) is used, the dose can be halved as compared to that of a continuous X-ray. Also, the control unit in the operation console 3 may include a circuit for ON/OFF-controlling the radiation of an X-ray at a high speed, so that an operator may desirably turn on/off an X-ray at a high speed while maintaining the rotation of the X-ray tube 12 and the detector array 16 and the pre-heat state of the X-ray tube 12. With this arrangement, an X-ray can be easily frequently turned on/off at a high speed, and the exposure amount on an object to be examined can be decreased.

Figure 10:
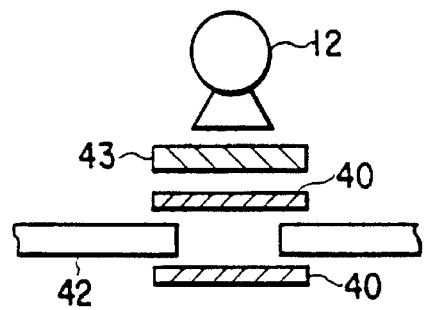
FIG. 10 is a sectional view showing a filter for decreasing the exposure amount.

Furthermore, as shown in FIG. 10, a filter 40 consisting of aluminum or copper may be arranged near an X-ray exit or an upper slit 42 of the X-ray tube 12, thereby decreasing the exposure amount on an object to be examined. The filter 40 may also consist of Teflon, molybdenum, or the like. Furthermore, the thickness of the filter 40 or a wedge 43 may be designed to be variable, thus allowing adjustment of the exposure amount during tomography.

In the above description, tomographic image data is not stored in the magnetic disk 38. However, a tomographic image displayed on the CRT monitor 7 may be stored using a video recorder, as needed. When a tomographic image is reproduced from the video recorder and is displayed after the end of the scan, the image may be displayed in units of frames or in the reverse direction, thus facilitating a diagnosis. Re-constructed image data and associated information may be recorded in a digital format. When recorded data is displayed, it is transferred to the CRT monitor 7 via the display memory 34. If image data is recorded as digital data, post-processing such as deletion of an image can be easily performed.

Second Embodiment

FIG. 11 shows the overall arrangement of a computer tomography apparatus according to the present invention.

An X-ray tube 51, a multi-channel X-ray detector 52, a rotary mechanism 53, an X-ray controller 57, a data acquisition unit 58, and a data acquisition controller 65 are housed in a frame. The rotary mechanism 53 can rotate the X-ray tube 51 and the multi-channel X-ray detector 52 while maintaining a state wherein they face each other to sandwich an object to be examined (patent) P therebetween. The X-ray tube 51 is electrically connected to the X-ray controller 57 present on a stationary portion via a slip ring mechanism, and the multi-channel X-ray detector 52 is electrically connected to the data acquisition unit 58 via the slip ring mechanism. With this arrangement, the X-ray tube 51 and the multi-channel X-ray detector 52 can acquire projection data while being continuously rotated through 360x or more. The X-ray controller 57 applies a tube voltage to the X-ray tube 51 to radiate X-rays. The data acquisition unit 58 repetitively acquires projection data via the multi-channel X-ray detector 52 at a period corresponding to the control of the data acquisition controller 65. A rotation controller 54 supplies driving electric power to the rotary mechanism 53 to rotate the X-ray tube 51 and the multi-channel X-ray detector 52. A couch has a top plate 55 on which the patient P is placed, and the top plate 55 is slidable along the longitudinal direction of the couch. A couch controller 56 supplies driving electric power to the couch to slide the top plate 55.

The system for rotating both the X-ray tube 51 and the multi-channel X-ray detector 52 is a system called R/R or the third generation. The present invention is not limited to this system, but may be applied to a system called R/S (fourth generation) in which the multi-channel X-ray detector 52 corresponding to one revolution around the object is fixed, and only the X-ray tube 51 is rotated.

Projection data acquired by the data acquisition unit 58 are supplied to a re-construction unit 63 via a memory 61 in units of channels, and are used for re-constructing a tomographic image. Note that the re-construction unit 63 has a function-performance for displaying tomographic images on an image display device 64 like cinema images while executing a continuous scan as in the first embodiment.

The rotation controller 54, the couch controller 56, the X-ray controller 57, and the data acquisition controller 65 are controlled by a scan controller 59 to execute a helical scan. The helical scan is a volume scan in which X-ray radiation and data acquisition are repeated while rotating the X-ray tube 51 and the multi-channel X-ray detector 52, and during this period, the patient P is continuously moved in one direction. Assuming a moving coordinate system which moves together with the patient P, since the X-ray tube 51 moves along a helical path, this volume scan is called the helical scan.

The scan controller 59 receives scan information such as an X-ray energy, a data acquisition period, and the like from a system controller 60 as a host computer, and also receives the start and end instructions of a continuous scan. The system controller 60 controls the re-construction unit 63. With this control, the re-construction unit 63 repetitively executes re-construction processing for a single tomographic image in synchronism with the scan operation, and sequentially supplies tomographic image data to the image display device 64 after an elapse of a predetermined period of time from the scan operation.

An input means 62 is connected to the scan controller 59. The input means 62 comprises, e.g., a touch switch or a push-button switch, i.e., is a switch which maintains an ON state while an operator depresses the switch, and is automatically restored to an OFF state when the operator releases the switch. When the input means 62 is in an ON state, the scan controller 59 performs a scan and acquires projection data. When the input means 62 is in an OFF state, the scan controller 59 stops X-ray radiation and data acquisition, but keeps rotation of the X-ray tube 51 and the multi-channel X-ray detector 52. With this control, immediately after the input means 62 is switched from an OFF state to an ON state again, the X-ray radiation can be started, and data acquisition can be started. When the rotation of the X-ray tube 51 and the multi-channel X-ray detector 52 is stopped while the input means 62 is in an OFF state, if the rotation of the X-ray tube 51 and the multi-channel X-ray detector 52 is started immediately after the input means 62 is switched to an ON state, a predetermined wait time is required until they reach a predetermined angular velocity.

The operation will be described below. FIG. 12 shows the helical path of the X-ray tube during a helical scan on the above-mentioned moving coordinate system. A bold line represents the ON period of the input means 62, and a thin line represents the OFF period of the input means 62. FIG. 13 is a timing chart showing the states of the rotation operation of the X-ray tube 51 in response to a change in state of the input means 62, the slide operation of the couch, the X-ray radiation operation, and the image re-construction operation.

At time t0, the X-ray tube 51 and the multi-channel X-ray detector 52 begin to rotate, and at the same time, the top plate 55 begins to slide. The rotation of the X-ray tube 51 and the multi-channel X-ray detector 52, and the sliding of the top plate 55 are continued independently of the ON/OFF state of the input means 62 until the top plate 55 reaches a planned last position. Assume that the input means 62 is in an OFF state in an initial state. When the input means 62 is in an OFF state, X-rays are not radiated, and data acquisition is not executed. When a region of interest of the patient P has reached a tomography region, an operator switches the input means 62 from an OFF state to an ON state. With this operation, the X-ray radiation is started under the control of the system controller 60, and acquisition of projection data is started. Since the X-ray tube 51 and the multi-channel X-ray detector 52 have been rotating at a constant speed before the input means 62 is switched to the ON state, when the input means 62 is switched to the ON state, the X-ray radiation can be immediately started to start data acquisition without waiting for an acceleration period required until the X-ray tube 51 and the multi-channel X-ray detector 52 in a stop state reach a predetermined angular velocity. While the input means 62 is kept in the ON state, the X-ray radiation and data acquisition are continued, and every time projection data for 360° or 180° required for re-constructing a single tomographic image are acquired, tomographic image data are sequentially re-constructed and are displayed on the image display device 64 as dynamic images like cinema images. When the input means 62 is switched to an OFF state, the X-ray radiation and data acquisition are stopped. However, the rotation of the X-ray tube 51 and the multi-channel X-ray detector 52, and the sliding of the top plate 55 are continued. When the input means 62 is switched to an ON state again, the X-ray radiation is immediately started as in the above operation to start data acquisition. Such an operation is repeated until the top plate 55 reaches a planned last position.

Furthermore, the rotation of the X-ray tube 51 and the multi-channel X-ray detector 52 is continued until the diagnosis is finished and an operator instructs the end of diagnosis, and the top plate 55 is reciprocally moved within a predetermined range. It is preferable to perform such control of the system controller 60 for re-doing a scan or for repetitively observing an identical portion to be diagnosed.

Once the input means 62 is turned on even for a short period of time, the scan controller 59 controls to continue the X-ray radiation and data acquisition until projection data for 360° or 180° required for re-constructing at least one tomographic image data are acquired. With this control, an operator need not switch the input means 62 to an OFF state while determining the timing corresponding to one revolution or half a revolution of the X-ray tube 51.

As described above, according to this embodiment, X-ray radiation can be irradiated onto only a specific portion to acquire projection data by turning on/off the input means 62 while continuing a helical operation, and tomographic images of the portion can be observed in real time. Therefore, a problem of exposure due to unnecessary X-ray radiation can be solved. Since the rotation of the X-ray tube 51 and the multi-channel X-ray detector 52 is continued even when data acquisition is not performed, data acquisition can be started by only starting the X-ray radiation, and tomographic images of a region of interest can be reliably acquired. Furthermore, since the X-ray radiation is performed only when it is required, a finite radiation time due to a limitation on the heat capacity of the X-ray tube 51 can be efficiently utilized. In the above description, the helical scan has been exemplified. Of course, this embodiment can be applied to a continuous scan at an identical position, which is attained by continuously rotating the X-ray tube 51 and the multi-channel X-ray detector 52 while the top plate 55 stands still.

Third Embodiment

Figure 14:
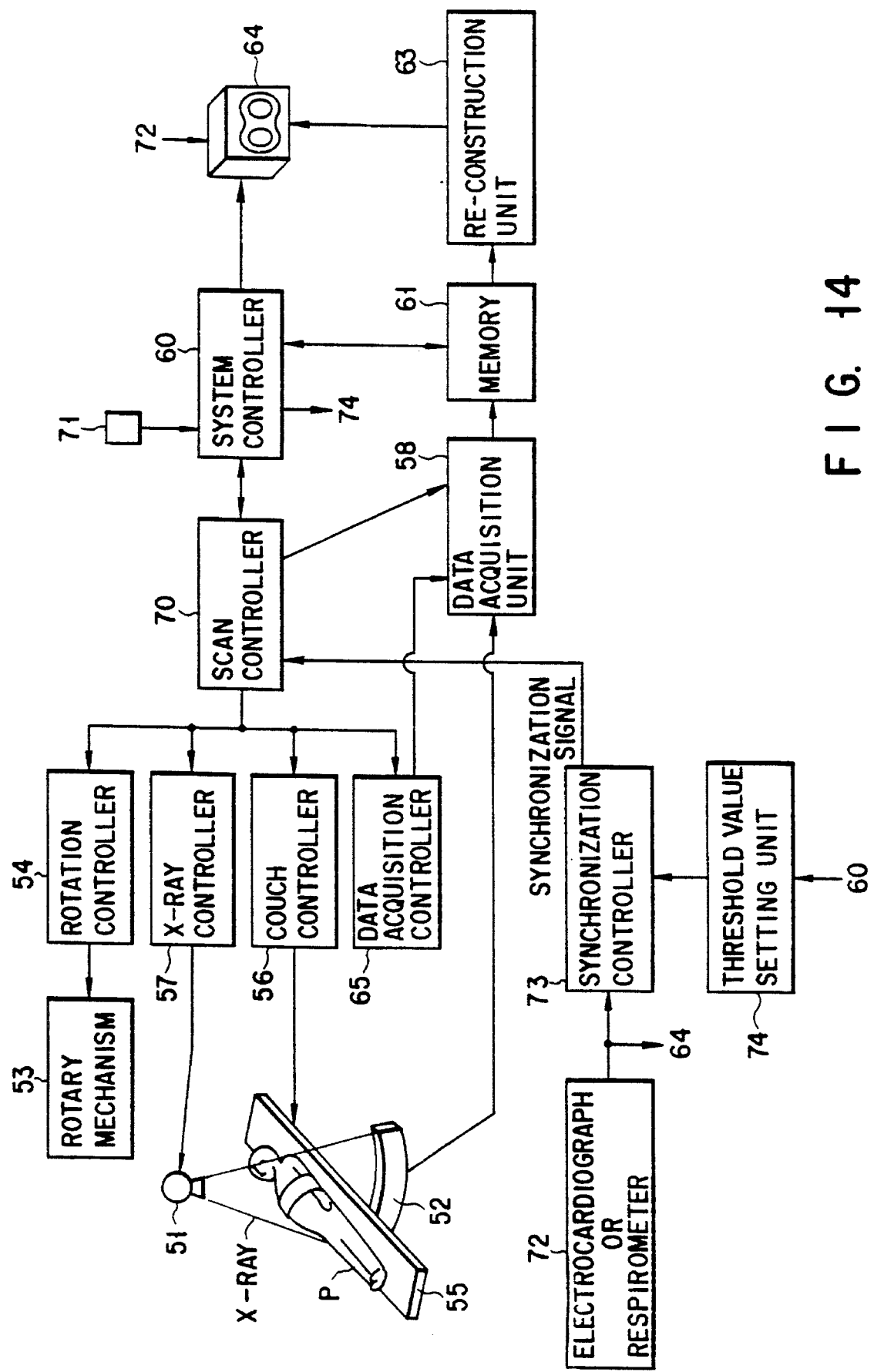
FIG. 14 is a block diagram showing the arrangement of the third embodiment.

The third embodiment will be described below. FIG. 14 is a block diagram showing the arrangement of a computer tomography apparatus of the third embodiment. The same reference numerals in FIG. 14 denote the same parts as in FIG. 11, and a detailed description thereof will be omitted. This embodiment assumes, in place of a helical scan, a single-slice scan which is attained by continuously rotating the X-ray tube 51 and the multi-channel X-ray detector 52 while the top plate 55 stands still, thereby realizing acquisition of tomographic image data corresponding to a specific heartbeat phase or respiration phase which is important for diagnosis.

A heartbeat waveform signal which represents a change in heartbeat of the patient P over time or a respiration waveform signal which represents a change in respiration over time is fetched by a synchronization controller 73 via an electrocardiograph or respirometer 72. The synchronization controller 73 recognizes a specific heartbeat phase or respiration phase on the basis of the heartbeat waveform signal or respiration waveform signal. This recognition is attained by comparing the heartbeat waveform signal or respiration waveform signal with a threshold value (specific amplitude) from a threshold value setting unit 74. The threshold value of the threshold value setting unit 74 is adjusted by the system controller 60 via an input means 71 such as a push-button switch. This adjustment will be described in detail later.

The synchronization controller 73 outputs a synchronization signal to a scan controller 70 at a timing when it recognizes the specific heartbeat phase or respiration phase. The scan controller 70 starts X-ray radiation at the reception timing of the synchronization signal, and continues the X-ray radiation for, e.g., 1 sec until projection data for 360° or 180° required for re-constructing single tomographic image data are acquired. The scan controller 70 controls to continue the continuous rotation of the X-ray tube 51 and the multi-channel X-ray detector 52 even when neither X-ray radiation nor data acquisition are performed.

The projection data for 360° or 180° acquired by the data acquisition unit 58 are supplied to the re-construction unit 63 via the memory 61. The re-construction unit 63 re-constructs tomographic image data on the basis of the received data. The tomographic image data is displayed on the image display device 64.

The operation of this embodiment will be described below. A specific heartbeat phase or respiration phase (threshold value) is set as follows. A region of interest of the patient P is set in a tomography region by sliding the top plate 55. A continuous scan is executed, and tomographic image data are displayed in real time as dynamic images like cinema images. At this time, the electrocardiograph or respirometer 72 is set in an active state, and a heartbeat waveform signal or respiration waveform signal during the continuous scan is fetched and held by the synchronization controller 73. An operator depresses the input means 71 at the display timing of a desired tomographic image while observing dynamic images. The system controller 60 designates the tomographic image displayed when the input means 71 is depressed. As has been described in the first embodiment, a predetermined time difference is present between the scan operation and the display of a tomographic image. Therefore, the system controller 60 supplies data of a time a predetermined period of time before the display time of the designated tomographic image to the threshold value setting unit 74. The threshold value setting unit 74 sets an amplitude at the time supplied from the system controller 60 as a threshold value for the held heartbeat waveform signal or respiration waveform signal. This threshold value signal is supplied to the synchronization controller 73.

Alternatively, a specific heartbeat phase or respiration phase may be set as follows. In this method, a heartbeat waveform signal or respiration waveform signal is displayed on the image display device 64, as shown in FIG. 15A or 15B. In this case, a threshold value Th is input on the screen by operating the input means 71 as a mouse or joystick, and data of the threshold value Th is supplied from the system controller 60 to the threshold value setting unit 74. The threshold value setting unit 74 D/A-converts the threshold value data to generate a threshold value signal, and supplies the signal to the synchronization controller 73.

After the threshold value is set, as described above, an operation for acquiring only a tomographic image corresponding to the specific heartbeat phase or respiration phase is started. The electrocardiograph or respirometer 72 is set in an active state, and a heartbeat waveform signal or respiration waveform signal is fetched by the synchronization controller 73. The rotation of the X-ray tube 51 and the multi-channel X-ray detector 52 is started, and constant-speed rotation is continued until the end of diagnosis is instructed.

The synchronization controller 73 compares the heartbeat waveform signal or respiration waveform signal with the threshold value signal from the threshold value setting unit 74, and outputs a synchronization signal to the scan controller 70 at each timing at which the amplitude of the signal has reached the threshold value. The scan controller 70 starts the X-ray radiation and data acquisition at reception timings t1, t2, ... of the synchronization signal. The. X-ray radiation and data acquisition are continued from each of times t1, t2, ... until projection data for 360° or 180° required for re-constructing at least one tomographic image are acquired. During time periods other than the above-mentioned times, the rotation of the X-ray tube 51 and the multi-channel X-ray detector 52 is continued, but the X-ray radiation and data acquisition are not performed. The projection data for 360° or 180° intermittently acquired at times t1, t2, ... by the data acquisition unit 58 are supplied to the re-construction unit 63 via the memory 61, and tomographic image data are sequentially re-constructed. The tomographic image data are displayed in real time after an elapse of a predetermined period of time from times t1, t2, ....

As described above, according to this embodiment, only tomographic images corresponding to a specific heartbeat phase or respiration phase are displayed as dynamic images. Since X-rays are not radiated during a period other than the periods required for acquiring projection data necessary for re-constructing the tomographic images, the exposure amount can be reduced, and a limited continuous radiation time due to the heat capacity of the X-ray tube can be efficiently utilized.

Fourth Embodiment

Figure 16:
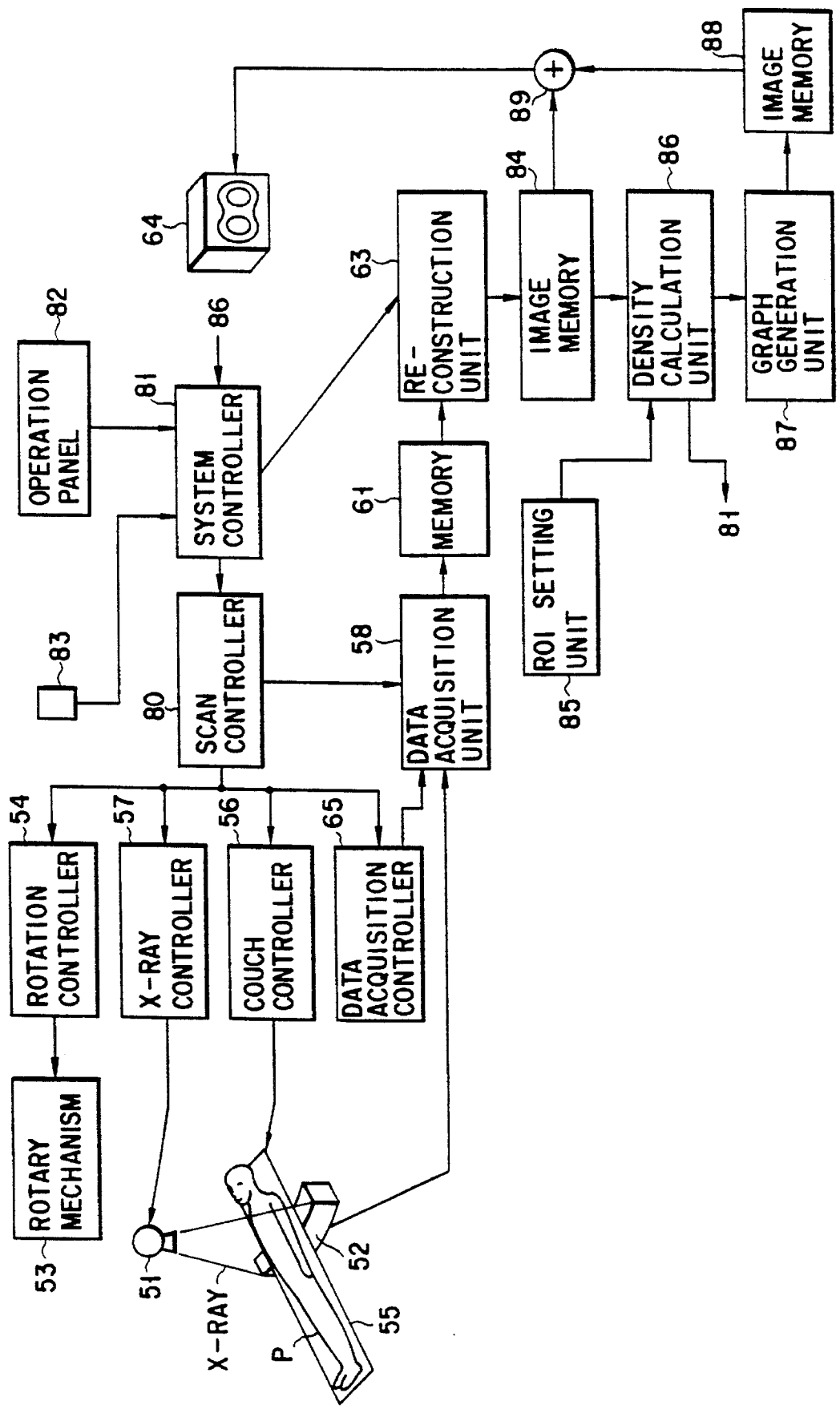
FIG. 16 is a block diagram showing the arrangement of the fourth embodiment.

FIG. 16 is a block diagram showing the arrangement of the fourth embodiment. The same reference numerals in FIG. 16 denote the same parts as in FIG. 11, and a detailed description thereof will be omitted. This embodiment relates to a technique for automating the execution timing of a scan in synchronism with the arrival of a contrast medium to a region of interest in an angiography. More specifically, the contrast medium density in an upstream region nearer the heart than the region of interest is monitored by a pre-scan (continuous scan), and a main scan is executed at the region of interest after an elapse of a predetermined wait time from when the contrast medium density in the upstream region has reached a predetermined value. The above-mentioned automation is realized by adjusting the wait time to be equal to a time required until blood reaches the region of interest from the upstream region.

An operation panel 82 and a push-button switch 83 are connected to a system controller 81 as a host computer. An operator inputs, via the operation panel 82, various condition data such as the position of a pre-scan (upstream region), the scan condition of the pre-scan, the range of a main scan (region of interest: ROI), the scan condition of the main scan, the wait time, and the like. The operator observes a density graph (to be described later) during the pre-scan, and depresses the push-button switch 83 when the density has reached a predetermined value. At the depression timing of the push-button switch 83, the pre-scan ends and preparation for the main scan is started.

Projection data acquired by the data acquisition unit 58 are supplied to the re-construction unit 63 via the memory 61. Tomographic image data re-constructed by the re-construction unit 63 are supplied to a density calculation unit 86 and an adder 89 via an image memory 84. The density calculation unit 86 adds CT values in an ROI set by an ROI setting unit 85. The CT value is proportional to the amount of the contrast medium. Therefore, the sum value includes information of the contrast medium density in the ROI. The sum value data is supplied to a graph generation unit 87. The graph generation unit 87 generates a graph representing a change in contrast medium density over time by plotting the sum value along the time base. The graph data is supplied to the adder 89 via an image memory 88. The adder 89 synthesizes the tomographic image data and the graph data on one screen, and supplies the synthesized data to the image display device 64.

Figure 17:
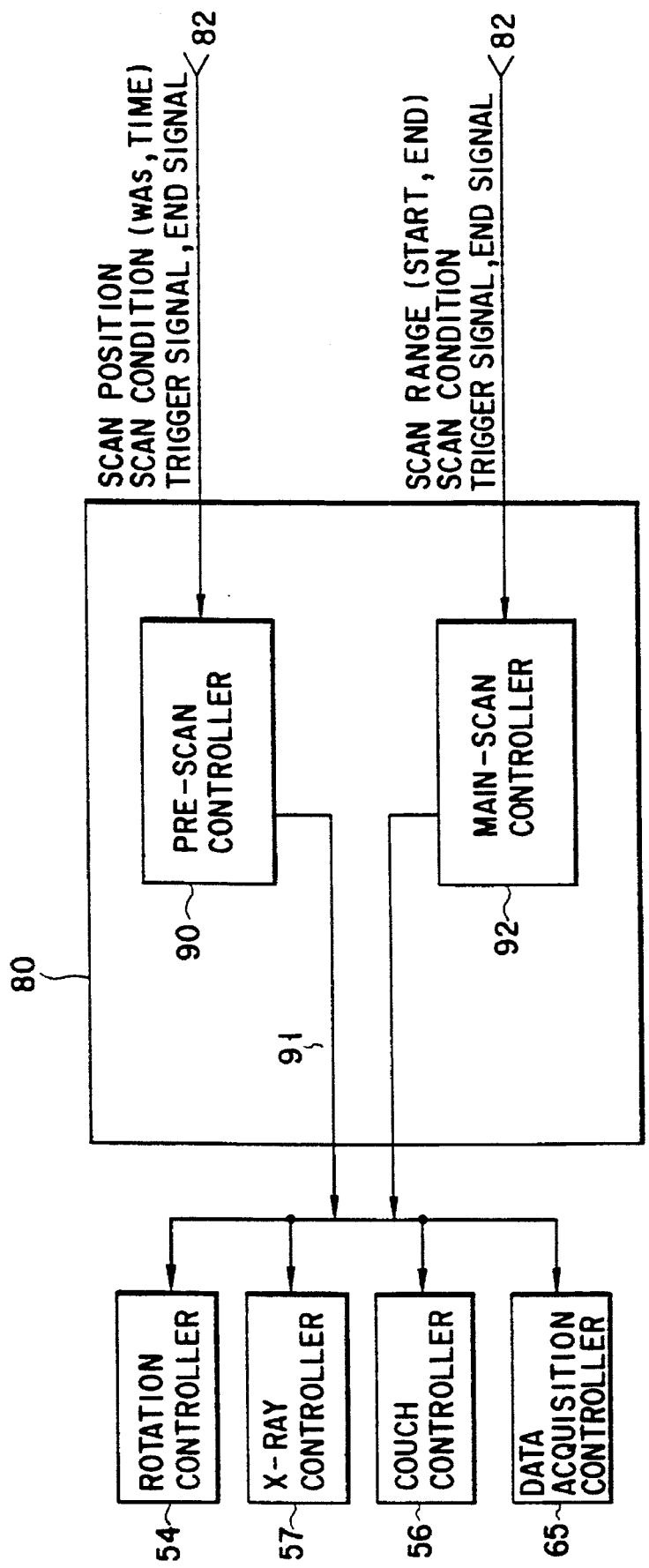
FIG. 17 is a block diagram of a scan controller shown in FIG. 16.

FIG. 17 is a block diagram of a scan controller 80 shown in FIG. 16. The scan controller 80 includes a pre-scan controller 90 for executing the pre-scan by controlling the units 54, 57, 56, and 65 associated with the scan, and a main scan controller 92 for executing the main scan by controlling the units 54, 57, 56, and 65 associated with the scan. The system controller 81 supplies, to the pre-scan controller 90, scan condition data such as data of the pre-scan position (the position of the top plate 55), the X-ray radiation condition (e.g., a tube voltage), the period of the data acquisition operation, and the like, a trigger signal indicating the start of the pre-scan, and an end signal indicating the end of the pre-scan. The system controller 81 supplies, to the main scan controller 92, scan condition data such as data of the range of the main scan (the start and end positions of the top plate 55), the X-ray radiation condition (e.g., a tube voltage), the period of the data acquisition operation, and the like, a trigger signal indicating the start of the main scan, and an end signal indicating the end of the main scan.

The operation of this embodiment will be described below. FIG. 18 is a timing chart for explaining the operation of this embodiment. FIG. 19 is a view showing the positions of the pre-scan and the main scan. In the following description, the contrast inspection of the head of a patient will be exemplified. In the case of the head inspection, the neck is normally selected as an upstream region.

Various condition data such as the pre-scan position (the upstream region; the neck in this case), the scan condition of the pre-scan, the main scan range (the region of interest; the head in this case), the scan condition of the main scan, the wait time from the end of the pre-scan to the beginning of the main scan, and the like are input via the operation panel 82. Then, the top plate 55 is slid, and is stopped at the pre-scan position.

Figure 20:
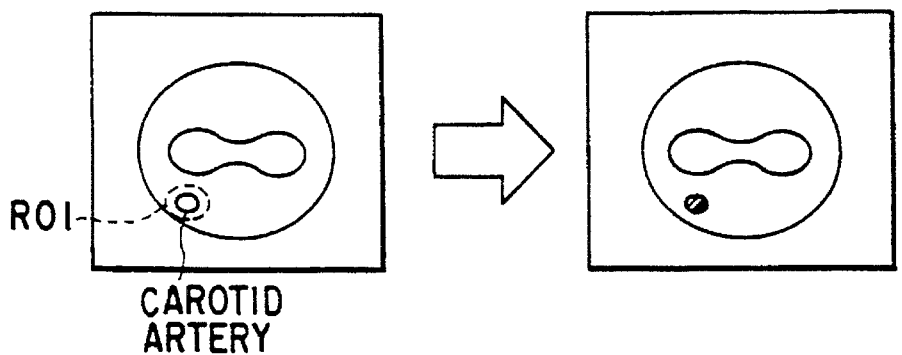
FIG. 20 is a view showing a change in contrast density on a tomographic image.
Figure 21:
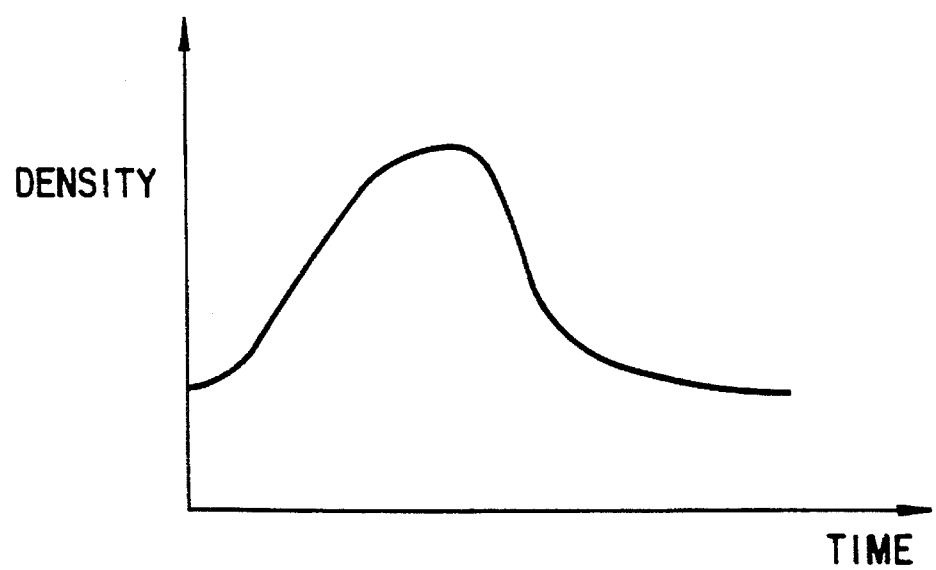
FIG. 21 is a graph showing a change in contrast density.

After the above-mentioned preparation is completed, a contrast medium is injected from, e.g., an arm vein. Thereafter, the system controller 81 supplies a trigger signal to the pre-scan controller 90 in response to an instruction from the operator. In response to this signal, the pre-scan is started. More specifically, the continuous rotation of the X-ray tube 51 and the multi-channel X-ray detector 52 is started, X-ray radiation is started, and data acquisition is started. With this pre-scan, tomographic image data of the upstream region are repetitively re-constructed by the re-construction unit 63. The re-constructed tomographic image data are supplied to the density calculation unit 86 and the adder 89 via the image memory 84. The density calculation unit 86 adds CT values in an ROI set on the carotid artery via the ROI setting unit 85, as shown in, e.g., FIG. 20. Note that the upstream region is not limited to the neck, and can be set anywhere as long as it is at the upstream side of the region of interest (head). However, the neck is suitably set as the upstream region since the time required for the blood flow to reach the head from the neck suffers a relatively small personal difference. The sum value data is sequentially supplied to the graph generation unit 87. The graph generation unit 87 generates a density graph, as shown in FIG. 21. The graph data is supplied to the adder 89 via the image memory 88, and is synthesized with tomographic image data on one screen. The synthesized data is displayed on the image display device 64. The graph data is sequentially updated for each scan of a single tomographic image together with the tomographic image data.

The operator observes the density graph during the pre-scan, and depresses the push-button switch 83 when the density has reached a predetermined value. Of course, the operator may determine the depression timing of the push-button switch 83 while observing the tomographic image. When the contrast medium flows into the carotid artery, the display density of the portion of the carotid artery increases, as shown in FIG. 21. At the depression timing of the push-button switch 83, the system controller 81 supplies an end signal to the pre-scan controller 90. The pre-scan controller 90 stops the X-ray radiation and data acquisition. In this case, the pre-scan controller 90 continues the rotation of the X-ray tube 51 and the multi-channel X-ray detector 52. Furthermore, the pre-scan controller 90 slides the top plate 55, and stops it at the main scan start position.

The main scan controller 92 waits for a trigger signal from the system controller 81 in this state. After an elapse of a predetermined wait time Δt from the depression timing of the push-button switch 83, the system controller 81 supplies a trigger signal to the main scan controller 92. The main scan controller 92 starts the main scan at the reception timing of the trigger signal. As the main scan, a helical scan is adopted in this case. Alternatively, a single-slice scan may be adopted. The X-ray tube 51 and the multi-channel X-ray detector 52 are kept rotated, the top plate 55 is slid at a constant speed toward the end position of the main scan, X-rays are radiated, and data acquisition is repeated. With this main scan, acquisition of projection data is started at an optimal timing at which the contrast medium begins to flow into the region of interest. This scan is repeated until the top plate 55 reaches the end position. During this interval, a tomographic image is re-constructed each time projection data required for re-constructing a single tomographic image are acquired, and is displayed as a dynamic image.

As described above, according to this embodiment, after the contrast medium is injected, the operator need only depress the push-button switch 83 while observing the density graph, resulting in a very simple operation. In addition, a tomographic image at an optimal contrast medium density can be obtained without a failure. Also, the exposure amount can be prevented from increasing when the scan is started too early for fear of failure in obtaining a tomographic image at an optimal contrast medium density.

Figure 22:
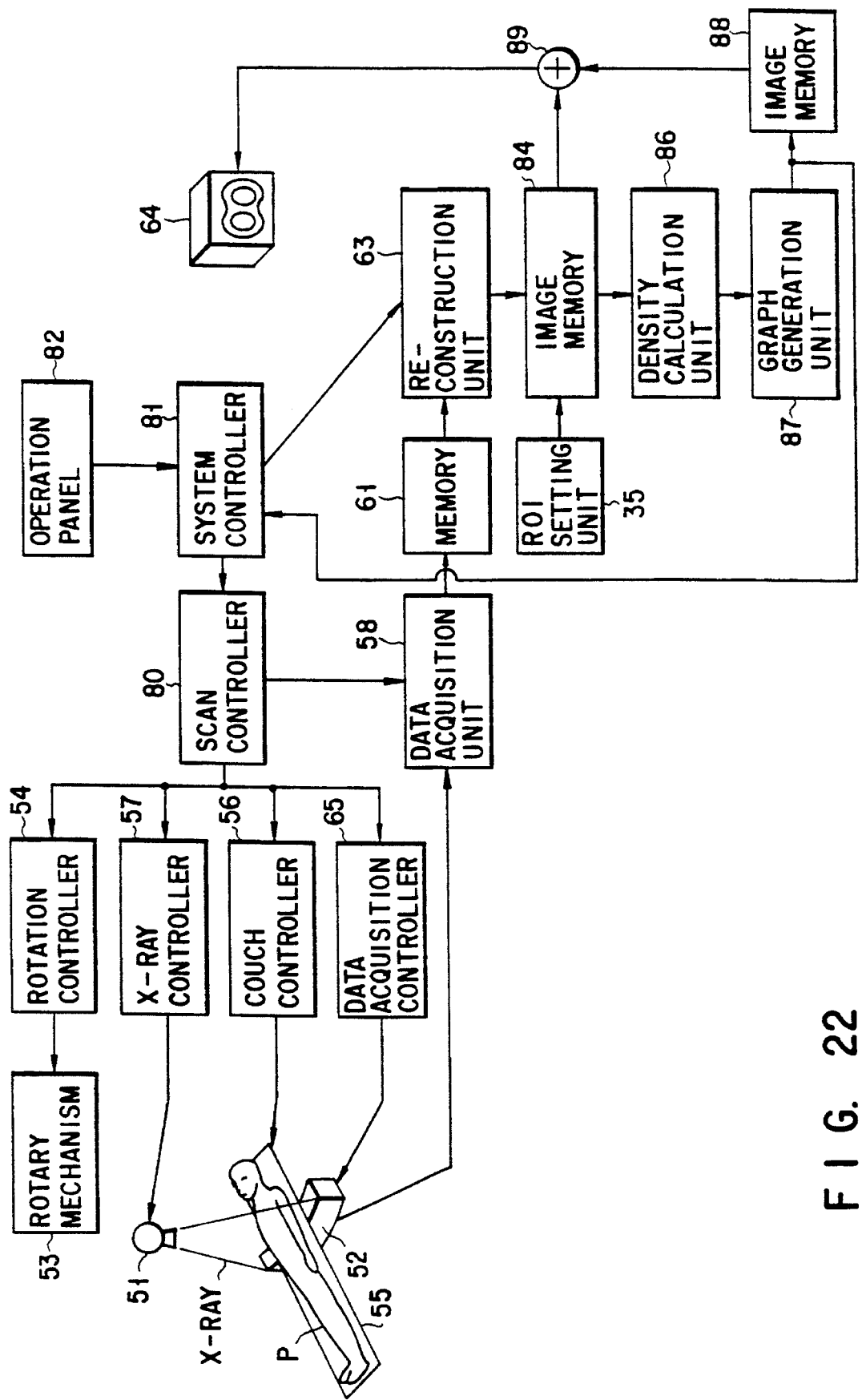
FIG. 22 is a block diagram showing the arrangement of a modification of the fourth embodiment.
Figure 23A:
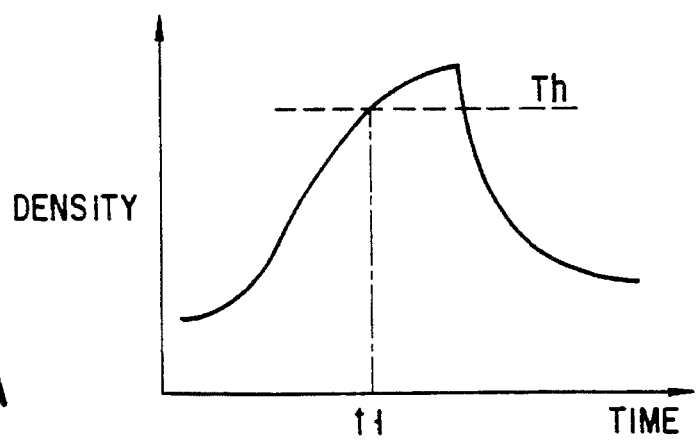
FIGS. 23A to 23C are explanatory views of a method of discriminating the end of a pre-scan.
Figure 23B:
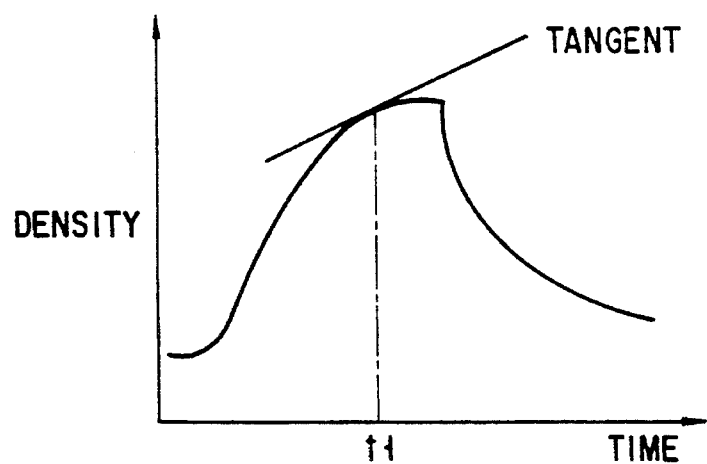
Figure 23C:
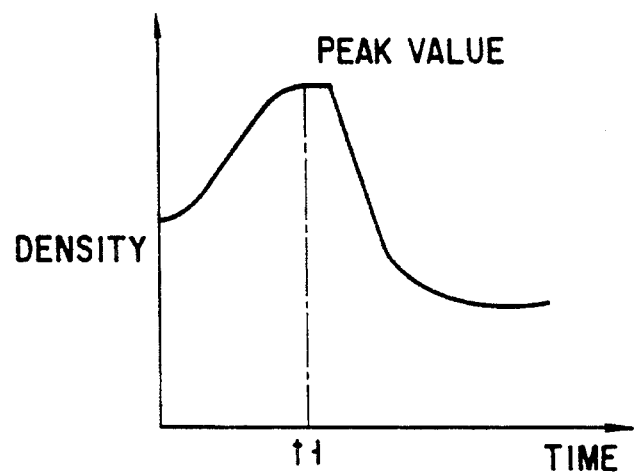

In the above description, the operator who depresses the push-button switch 83 discriminates whether or not an optimal density is reached in the upstream region, but this discrimination can be easily automated. As shown in FIG. 22, the system controller 81 fetches the data of the density graph generated by the graph generation unit 87, and makes the above-mentioned discrimination on the basis of the density graph. As the discrimination method, the following methods are provided. In the first method, as shown in FIG. 23A, time t1 at which the graph has reached a threshold value corresponding to an optimal density is discriminated as the depression timing of the push-button switch 83. In the second method, time t1 at which the inclination of the tangent to the graph has reached a predetermined value is discriminated as the depression timing of the push-button switch 83. In the third method, time t1 at which the graph has reached a peak value (maximal value) is discriminated as the depression timing of the push-button switch 83. Furthermore, as another method of discriminating an optimal density in an upstream region, the following method is provided.

Figure 24:
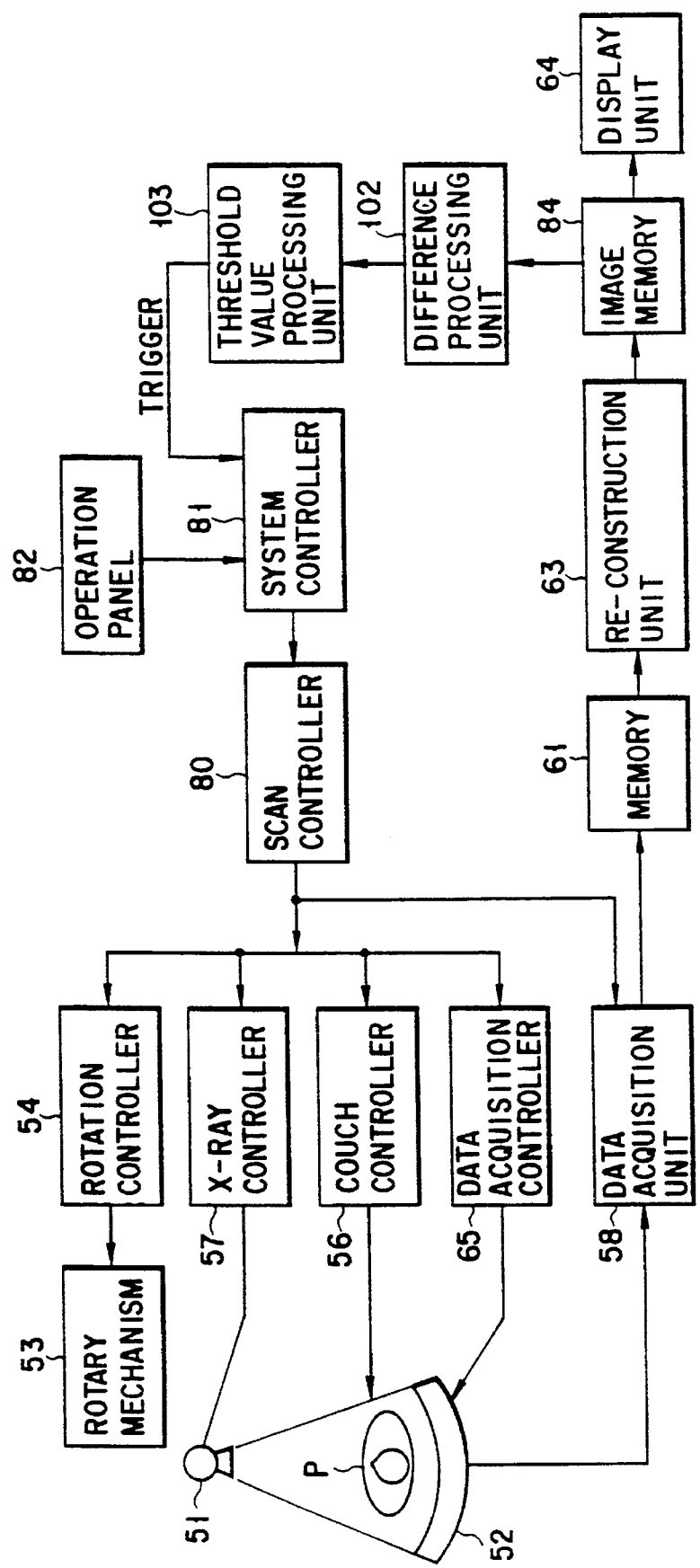
FIG. 24 is a block diagram showing the arrangement of another modification of the fourth embodiment.
Figure 25:
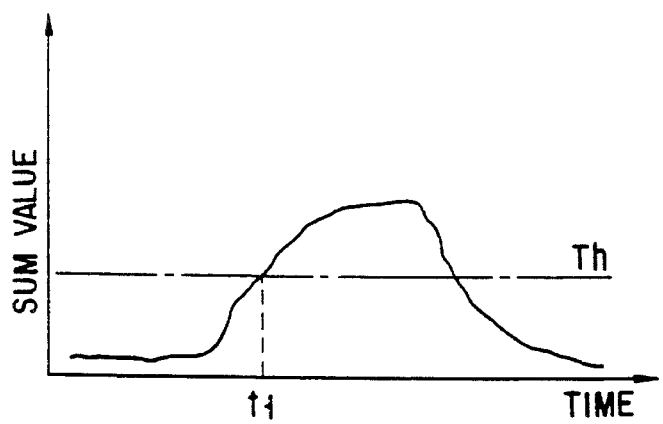
FIG. 25 is a graph showing a change in differential density.

FIG. 24 is a block diagram showing the arrangement corresponding to the fourth method. FIG. 25 shows a change in sum value over time. Tomographic image data re-constructed by the re-construction unit 63 are sequentially supplied to a difference processing unit 102 via the image memory 84. The difference processing unit 102 holds tomographic image (mask image) data before the contrast medium flows in. The difference processing unit 102 subtracts the mask image data from the tomographic image data in units of frames. Then, the unit 102 adds all pixel values of the difference image. This sum value is supplied to a threshold value processing unit 103, and is compared with a predetermined threshold value Th. The threshold value processing unit 103 discriminates time t1 at which the sum value has reached the threshold value Th as the depression timing of the push-button switch 83.

Figure 26:
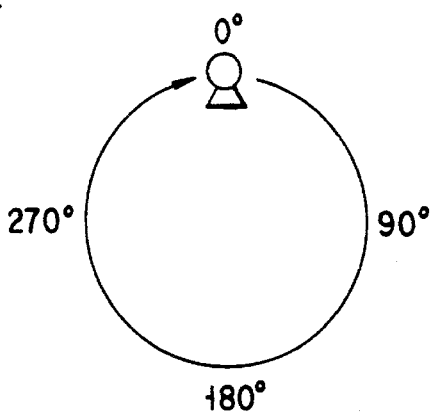
FIG. 26 is a view showing a change in angle of an X-ray tube.
Figure 27A:
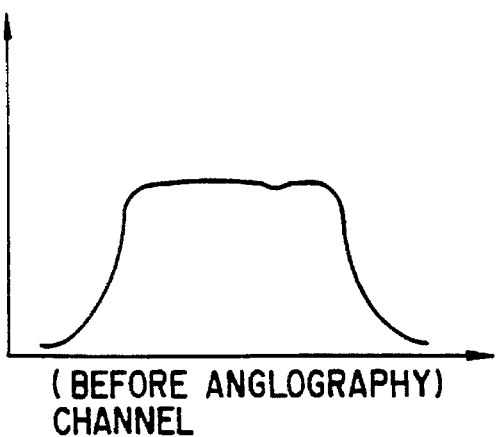
FIGS. 27A to 27C are explanatory views of another method of discriminating the end of a pre-scan.
Figure 27B:
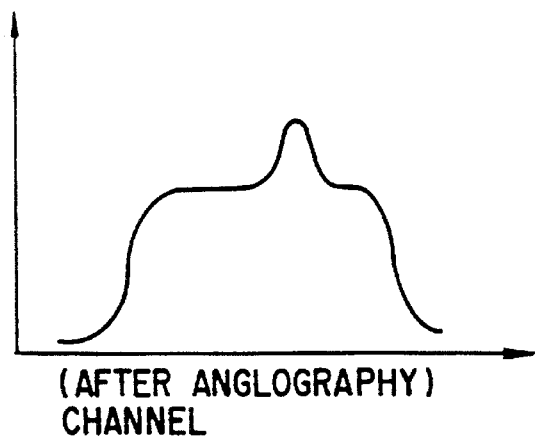
Figure 27C:
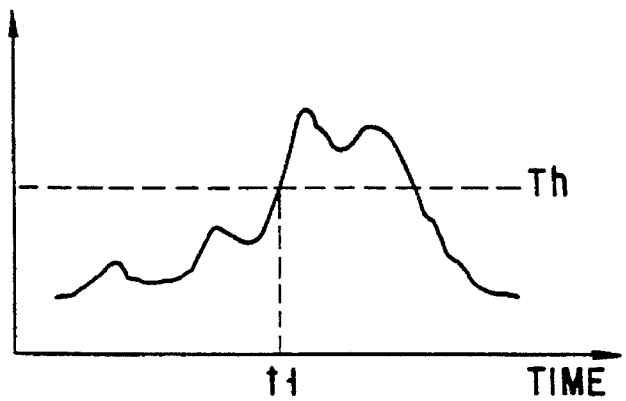

Furthermore, a modification for decreasing the exposure amount during the pre-scan is provided. As shown in FIG. 26, during the pre-scan, X-rays are radiated for a very short period of time under the control of the scan controller 80 only when the X-ray tube 51, which is being continuously rotated, has reached a predetermined angular position (e.g., 0° position) to execute data acquisition once. Therefore, each time the X-ray tube 51 completes one revolution, a set of projection data of the first to n-th channels are obtained. A profile obtained by distributing the projection data of the first to n-th channels in units of channels will be referred to as a projection data profile hereinafter. FIG. 27A shows the projection data profile before the contrast medium flows in, and FIG. 27B shows the projection data profile at a given time after the contrast medium flows in. Since image re-construction need not be performed during the pre-scan, projection data acquired by the data acquisition unit 58 are fetched by the system controller 81 via the memory 61, and the system controller 81 makes the discrimination. The system controller 81 holds the projection data profile data before the contrast medium flows in. The system controller 81 subtracts the projection data profile before the contrast medium flows in from the projection data profile obtained during the pre-scan after the contrast medium flows in for each channel, and accumulates the difference values of all the channels, thus calculating a differential area. FIG. 27C shows a change in differential area over time. The system controller 81 discriminates time t1 at which the differential area has reached the threshold value Th as the depression timing of the push-button switch 83.

Fifth Embodiment

X-ray radiation accompanies heat generation. The amount of this heat generation is accumulated as the heat capacity in components constituting the X-ray tube 51. Most apparatuses which perform X-ray radiation have a safety function for forcibly setting the apparatuses in a system-down state before the heat capacity reaches a limit value. The computer tomography apparatus has this function as well. This embodiment prevents the apparatus from being set in a system-down state at an unexpected timing.

Figure 28:
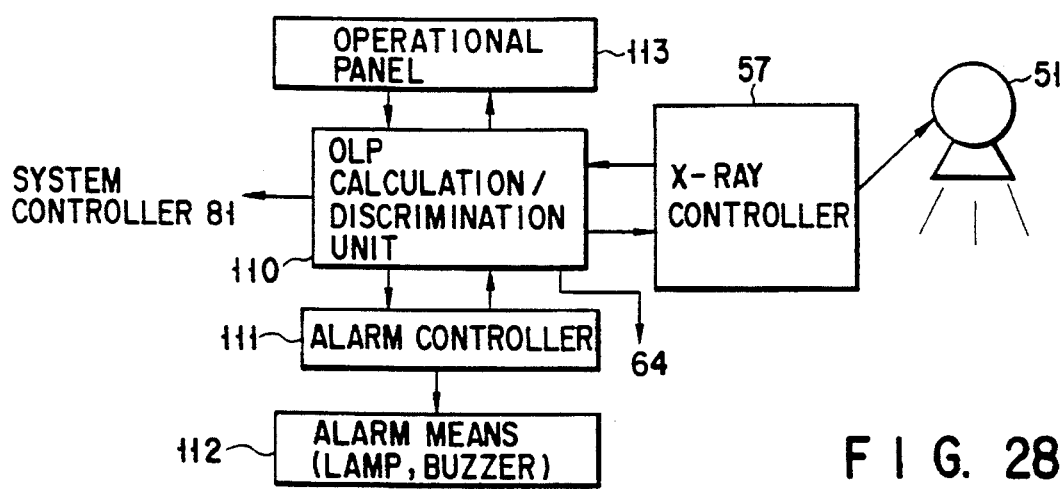
FIG. 28 is a block diagram showing principal part of the fifth embodiment.

FIG. 28 is a block diagram showing principal part of this embodiment. Scan conditions are input from an operation panel 113. Of the scan conditions, data such as a tube voltage, tube current, and the like, which are required for calculating the heat capacity are supplied to an OLP calculation/discrimination unit 110. Alternatively, data of an actual tube voltage and tube current to be actually supplied from the X-ray controller 57 to the X-ray tube 51 may be supplied to the OLP calculation/discrimination unit 110. Note that "OLP" is an abbreviation for overload protection management. The OLP calculation/discrimination unit 110 repetitively calculates the remaining time until a system-down state at a predetermined period. If the calculation period is represented by T2, and the tube voltage, tube current, and heat conversion constant are respectively represented by V, A, and R, a heat capacity $\Delta H$ supplied during the period T2 is given by:

$$\Delta H = V \cdot A \cdot R \cdot T2$$

In the n-th calculation period after the continuous scan is started, a remaining time TR is given by:

$$TR = ((H0 - (n+1) \cdot \Delta H)/\Delta H) \cdot T2$$

Figure 29A:
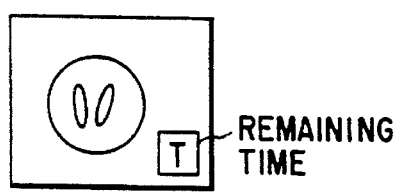
FIGS. 29A and 29B are views showing the display screen.

The data of the calculated remaining time TR is supplied from the system controller 81 to the image display device 64, and is displayed together with a tomographic image, as shown in FIG. 29A. Note that the system controller 81 may begin to display the remaining time TR when the remaining time TR becomes shorter than a predetermined time. In this case, the display of the remaining time TR also serves as an alarm message indicating that the remaining time becomes short.

Note that the period T2 is a calculation period and is also a display switching period. As can be seen from the above equation, the remaining time TR corresponding to the (n+1)-th period is calculated. This is to display the precise remaining time TR at the time of display. If the remaining time TR at the n–th calculation period is calculated by:

$$TR = ((H0 - n \cdot \Delta H)/\Delta H) \cdot T2$$

Figure 30:
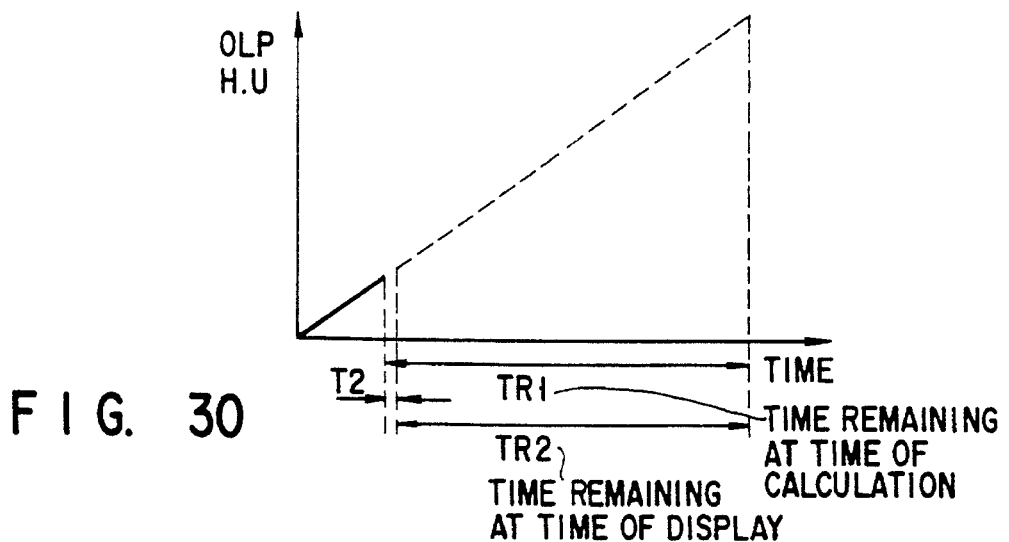
FIG. 30 is a graph showing two different remaining timings in comparison with each other.

TR1 includes an error corresponding to one period T2 as compared to the true remaining time TR2 at the time of actual display, as shown in FIG. 30.

Figure 29B:
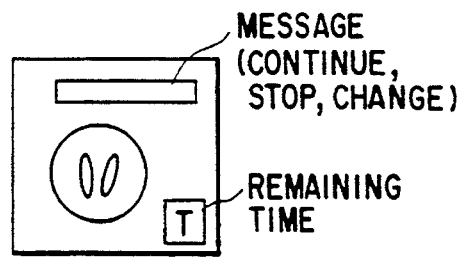

The OLP calculation/discrimination unit 110 is connected to an alarm means 112 via an alarm controller 111. When the remaining time TR becomes shorter than a predetermined time, the OLP calculation/discrimination unit 110 controls the alarm controller 111 to start the alarm means 112, and generates an alarm indicating that the remaining time has become short to an operator. The alarm means 112 comprises a lamp or buzzer, and an alarm is provided by turning on the lamp or generating an alarm tone. Furthermore, it is effective and preferable in the sense of emphasizing a decrease in remaining time to change an alarm mode by changing the color of the lamp or changing the pitch or tone volume of the alarm tone each time the remaining time TR reaches each of stepwise alarm times. Also, it is preferable to display alarm messages "continue", "stop", "change", and the like stepwise, as shown in FIG. 29B, each time the remaining time TR reaches each of stepwise alarm times. Note that "change" is a message for urging an operator to decrease the radiation conditions such as the tube current, tube voltage, and the like so as to decrease the X-ray energy, thereby prolonging the remaining time.

Figure 31:
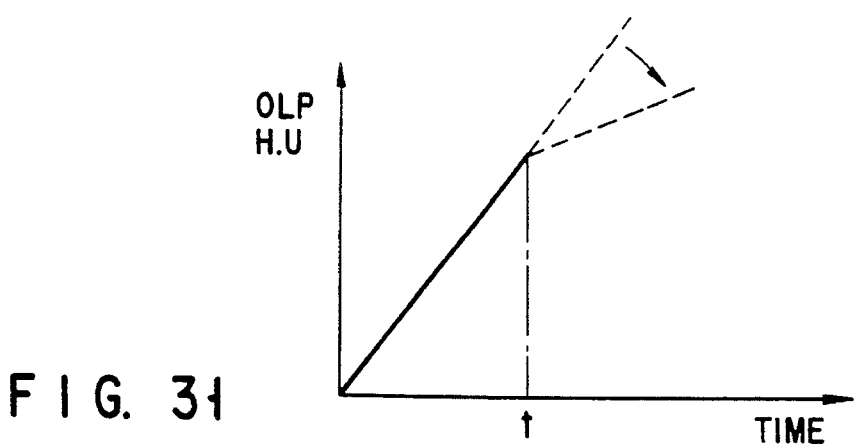
FIG. 31 is a graph showing a difference between changes in heat capacity of an X-ray tube when X-ray energy is lowered.
Figure 32:
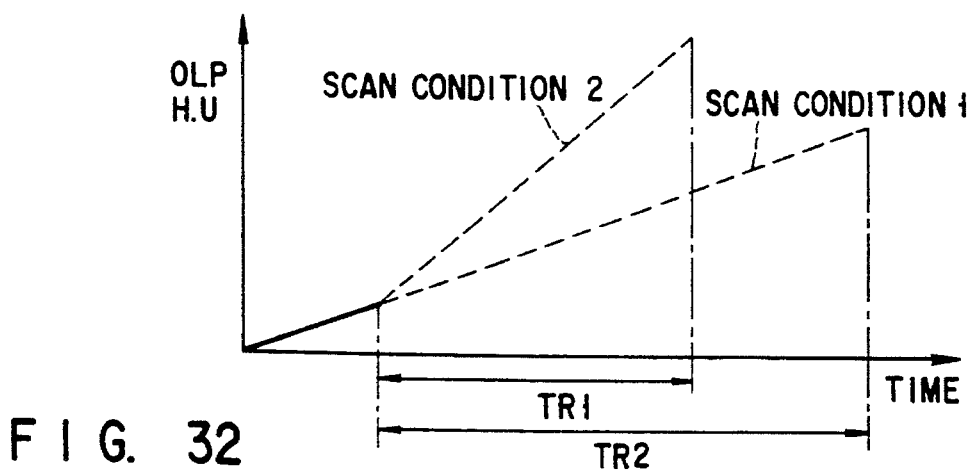
FIG. 32 is a graph showing a difference between changes in heat capacity of an X-ray tube under two different scan conditions.

When the tube current or tube voltage is changed during the continuous scan, the remaining time TR is calculated based on the changed tube current or tube voltage, as a matter of course. When the tube current or tube voltage is decreased, the heat capacity $\Delta H$ supplied during the period T2 decreases, and the remaining time is extended accordingly, as shown in FIG. 31. The tube current or tube voltage may be increased during the continuous scan when an X-ray of low energy is used during alignment, and an X-ray of high energy is used in an actual diagnosis to obtain a high-quality tomographic image. In such a case, the heat capacity $\Delta H$ supplied during the period T2 increases, and the remaining time is shortened accordingly, as shown in FIG. 32. Condition 1 in FIG. 32 represents a condition for an X-ray of low energy, and condition 2 represents a condition for an X-ray of high energy.

It is effective to pre-set tube currents and tube voltages to be changed in the system controller, to calculate the remaining time corresponding to the current tube current and tube voltage and the remaining time corresponding to the changed tube current and tube voltage, and to display both the remaining times since the operator can determine the necessity of a change in tube current or voltage on the basis of the displayed times.

Sixth Embodiment

This embodiment has as its object to improve the patient throughput by shortening the examination time required per patient until the diagnosis is finally completed in such a manner that a given scanogram an X-ray projection image is imaged, a scan position is set on the basis of the scanogram, and a continuous scan is executed at this scan position.

FIG. 33 is a block diagram showing the arrangement of the sixth embodiment. The same reference numerals in FIG. 33 denote the same parts as in FIG. 11, and a detailed description thereof will be omitted. An X-ray tube 122 is designed to irradiate cone-shaped X-ray beam radiation onto a patient P. A two-dimensional X-ray detector array 123 is constituted by two-dimensionally arraying a plurality of X-ray detection elements. A scan controller 121 can operate in two different operation control modes, i.e., a scano mode and a continuous scan mode. In the scano mode, the scan controller 121 controls the rotation controller 54, the X-ray controller 57, the couch controller 56, and the data acquisition controller 65 to execute a scanogram imaging operation. In the continuous scan mode, the scan controller 121 controls the rotation controller 54, the X-ray controller 57, the couch controller 56, and the data acquisition controller 65 to execute a continuous scan. The scan controller 121 is connected to a mode selection switch 120, and an operator instructs switching of the mode to the scan controller 121 via the mode selection switch 120.

FIG. 34 is a timing chart showing the operation of this embodiment. In FIG. 34, the setting operation of the scan position is omitted. The scano mode is selected via the mode selection switch 120. The X-ray tube 122 is continuously rotated while being kept facing the two-dimensional X-ray detector array 123. When the X-ray tube 122 is at a predetermined angle (e.g., 0°), X-ray pulses are radiated. In synchronism with this radiation, projection data are acquired. With this operation, the two-dimensional distribution, i.e., the scanogram, of the projection data is imaged. If a conventional linear X-ray detector is used, X-ray radiation and data acquisition must be repeated a plurality of number of times while sliding the top plate 55. However, in this embodiment, a scanogram having the same size as that imaged by the above-mentioned operation can be obtained by a single imaging operation, thus greatly shortening the time.

The scanogram data is displayed on the image display device 64 via the memory 61. When a scanogram in a range wide in the slice direction, e.g., a scanogram of the whole body is required, the two-dimensional X-ray detector array 123 is slid by the distance corresponding to the slice width while the X-ray tube 122 and the two-dimensional X-ray detector array 123 are kept rotated, and X-ray radiation and data acquisition are executed again at that position, as shown in FIG. 34. The scanogram data is supplied to and held in the memory 61. Such an operation is repeated a plurality of number of times (e.g., a total of four times), and scanogram data for four scans are held in the memory 61. The scanogram data for the four scans are read out in a coupled state, are supplied as single scanogram data to the image display device 64, and are displayed thereon. When the top plate 55 has a high slide speed, and completes sliding of the distance corresponding to the slice width of the two-dimensional X-ray detector array 123 during one revolution of the X-ray tube 122, if the imaging operation is repeated a plurality of number of times, as described above, the imaging operation can be repeated once per revolution of the X-ray tube 122, and the imaging time of the scanogram can be minimized, i.e., the imaging time of the scanogram can be suppressed to a minimum time required for the X-ray tube 122 to complete a plurality of revolutions.

The scanogram obtained as described above is displayed on the image display device 64. Note that the scan controller 121 continues the rotation of the X-ray tube 122 and the two-dimensional X-ray detector array 123 until the continuous scan ends even after the imaging operation of the scanogram ends.

An operator sets the scan position on the screen by operating an input means such as a mouse while observing the scanogram. Upon completion of this setting operation, the operator operates the mode selection switch 120 to instruct execution of the continuous scan mode. The scan controller 121 slides the top plate 121 and stops it at the set scan position. The scan controller 121 starts X-ray radiation and data acquisition, and starts the continuous scan. Since the X-ray tube 122 and the two-dimensional X-ray detector array 123 are already rotated at a constant speed, the continuous scan can be started without any wait time immediately after the top plate 55 stops at the scan position.

As described above, according to this embodiment, the examination time required per patient can be shortened, thus improving the patient throughput.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A computer tomography apparatus which can perform an angiography, comprising:

an X-ray tube which is supported to be continuously rotatable around an object to be examined;

rotation control means for controlling rotation of said X-ray tube;

X-ray control means for controlling X-ray radiation from said X-ray tube;

data acquisition means, arranged to face said X-ray tube to sandwich the object to be examined therebetween, for acquiring projection data on the basis of an X-ray transmitted through the object to be examined;

re-construction means for re-constructing tomographic image data on the basis of the projection data acquired by said data acquisition means;

display means for displaying the re-constructed tomographic image data; and control means for controlling said rotation control means, said X-ray control means, said data acquisition means, and couch control means to execute a pre-scan at a first scan position, and controlling said rotation control means, said X-ray control means, said data acquisition means, and the couch control means to execute a main scan at a second scan position at a downstream of the first scan position, in which said control means starts the main scan after an elapse of a time required for a blood flow to reach the second scan position from the first scan position after the end of the pre-scan.

2. An apparatus according to claim 1, in which said control means controls said rotation control means to continue rotation of said X-ray tube until the pre-scan and the main scan end.

3. An apparatus according to claim 1, further comprising: graph generation means for generating a graph representing a change in density in an ROI of the tomographic image data over time during the pre-scan, in which said display means displays the graph on a single screen together with the tomographic image data.

4. An apparatus according to claim 1, further comprising: input means for instructing end of the pre-scan when an operator determines that a density of a contrast medium has reached a predetermined density while observing a tomographic image displayed on said display means.

5. An apparatus according to claim 1, further comprising: discrimination means for discriminating if a density in an ROI of the tomographic image data reaches a predetermined density during the pre-scan, in which said control means controls said X-ray control means and said data acquisition means to end the pre-scan when said discrimination means makes the discrimination.

6. An apparatus according to claim 5, in which said discrimination means discriminates whether or not a total value of a plurality of pixels in the ROI reaches the predetermined density.

7. An apparatus according to claim 5, further comprising: graph generation means for generating a graph representing a change in density in the ROI of the tomographic image data over time during the pre-scan, in which said discrimination means discriminates whether or not an inclination of a tangent to the graph reaches a predetermined inclination corresponding to the predetermined density.

8. An apparatus according to claim 5, in which said control means controls said X-ray control means to radiate an X-ray only when said X-ray tube is at a specific angle, and said discrimination means discriminates whether or not a difference value between projection data obtained at the specific angle before the angiography and projection data obtained at the specific angle after the angiography reaches the predetermined density.

9. An apparatus according to claim 5, in which said discrimination means discriminates whether or not a difference value between tomographic image data before the angiography and tomographic image data after the angiography reaches the predetermined density.

10. A computer tomography apparatus according to claim 1, further comprising:

measuring means for measuring one of a heartbeat waveform signal and a respiration waveform signal of the object to be examined; and second control means for controlling said rotation control means to continuously rotate said X-ray tube, and controlling said X-ray control means to radiate an X-ray in a specific phase in association with one of the heartbeat waveform signal and the respiration waveform signal.

11. An apparatus according to claim 10, in which said re-construction means re-constructs the tomographic data each time projection data required for re-constructing single tomographic image data are acquired, and said display means displays the tomographic image data after an elapse of a predetermined time from acquisition of the projection data.

12. An apparatus according to claim 10, in which said second control means controls said X-ray control means to continue X-ray radiation until projection data required for re-constructing at least one tomographic image data are acquired.

13. An apparatus according to claim 10, in which said second control means discriminates the specific phase by comparing an amplitude value of one of the heartbeat waveform signal and the respiration waveform signal with a predetermined threshold value.

14. A computer tomography apparatus according to claim 1, further comprising:

remaining time calculation means for calculating a remaining time until said X-ray tube reaches a limit heat capacity when X-ray radiation is continued with a current X-ray energy; and second display means for displaying the remaining time.

15. An apparatus according to claim 14, further comprising:

means for starting display of the remaining time when the remaining time becomes shorter than a predetermined time.

16. An apparatus according to claim 14, further comprising:

alarm means for turning on a lamp or generating a tone; and control means for controlling said alarm means to turn on the light or to generate the tone when the remaining time becomes shorter than a predetermined time.

17. An apparatus according to claim 14, further comprising:

control means for controlling said second display means to display a first message when the remaining time becomes shorter than a first time, and to display a second message when the remaining time becomes shorter than a second time shorter than the first time.

18. An apparatus according to claim 14, which said remaining time calculation means calculates the time remaining at the time of display on said second display means.

19. An apparatus according to claim 14, in which said remaining time calculation means calculates the remaining time corresponding to the current X-ray energy and another remaining time corresponding to another X-ray energy, and said second display means displays both the remaining time and the other remaining time.

20. A computer tomography apparatus according to claim 1, wherein said X-ray tube radiates a cone-shaped X-ray beam, further comprising:

a two-dimensional detector array comprising a plurality of acquisition elements arranged to face said X-ray tube with the object to be examined sandwiched between said array and said X-ray tube, said acquisition elements acquiring projection data on the basis of an X-ray transmitted through the object to be examined; and second control means for executing a first mode for imaging a scanogram and a second mode for executing a scan in turn, for controlling said rotation control means to rotate said X-ray tube and controlling said X-ray control means to radiate the X-ray when said X-ray tube is at a specific angle in the first mode, for controlling said rotation control means to rotate said X-ray tube and controlling said X-ray control means to continuously radiate the X-ray in the second mode, and for controlling said rotation control means to continue rotation of said X-ray tube even while an operation mode is switched from the first mode to the second mode.

21. An apparatus according to claim 20, further comprising:

a couch for slidably supporting a top plate on which the object to be examined is placed; and couch control means for controlling a sliding operation of said top plate;

said second control means, when operating in the first mode, obtaining a plurality of scanograms by controlling said rotation control means to continuously rotate said X-ray tube, controlling said X-ray control means to repeat X-ray radiation when said X-ray tube is at the specific angle, and controlling said couch control means to intermittently move said top plate by a predetermined distance equal to a slice width of said two-dimensional detector array in synchronism with the X-ray radiation to obtain said plurality of scanograms, Which are coupled to said display means; and said display means displaying the coupled scanograms as one scanogram.

22. A apparatus according to claim 21, wherein said second control means controls said couch control means so that said top plate completes a sliding operation of the predetermined distance while said X-ray tube completes one revolution to have the specific angle as a start point.

* * * * *